United States Patent
Gerber et al.

(10) Patent No.: US 10,308,972 B2
(45) Date of Patent: Jun. 4, 2019

(54) WHOLE-CELL SYSTEM FOR CYTOCHROME P450 MONOOXYGENASES BIOCATALYSIS

(71) Applicant: Sanofi, Paris (FR)

(72) Inventors: Adrian Gerber, Saarbrücken (DE); Frank Hannemann, Saarbrücken (DE); Sabrina Bleif, Staufen (CH); Michael Kleser, Völklingen (DE); Rita Bernhardt, Saarbrücken (DE)

(73) Assignee: SANOFI CHIMIE, Gentilly (FR)

( * ) Notice: Subject to any disclaimer, the term of this patent is extended or adjusted under 35 U.S.C. 154(b) by 0 days.

(21) Appl. No.: 14/898,655

(22) PCT Filed: Jun. 17, 2014

(86) PCT No.: PCT/EP2014/062749
§ 371 (c)(1),
(2) Date: Dec. 15, 2015

(87) PCT Pub. No.: WO2014/202627
PCT Pub. Date: Dec. 24, 2014

(65) Prior Publication Data
US 2016/0376625 A1    Dec. 29, 2016

(30) Foreign Application Priority Data

Jun. 17, 2013  (EP) ................................. 13305814

(51) Int. Cl.
| | | |
|---|---|---|
| C12P 33/16 | (2006.01) | |
| C12P 33/00 | (2006.01) | |
| C12N 1/21 | (2006.01) | |
| C12N 9/02 | (2006.01) | |
| C12P 7/62 | (2006.01) | |
| C12N 9/10 | (2006.01) | |

(52) U.S. Cl.
CPC ............ *C12P 33/16* (2013.01); *C12N 9/0081* (2013.01); *C12N 9/0095* (2013.01); *C12N 9/1029* (2013.01); *C12P 7/625* (2013.01); *C12P 33/00* (2013.01); *C12Y 114/15006* (2013.01); *C12Y 203/01* (2013.01)

(58) Field of Classification Search
None
See application file for complete search history.

(56) References Cited

U.S. PATENT DOCUMENTS

| 4,683,195 A | 7/1987 | Mullis et al. |
|---|---|---|
| 2003/0108982 A1 | 6/2003 | Slijkhuis et al. |
| 2010/0112634 A1 | 5/2010 | Spagnoli et al. |

FOREIGN PATENT DOCUMENTS

| EP | 0477961 A2 | 4/1992 |
|---|---|---|
| EP | 2386634 A1 | 11/2011 |
| JP | A1999308991 | 9/1999 |
| JP | A2004528827 | 9/2004 |
| RU | 2242517 | 12/2004 |
| SU | 1090716 | 5/1984 |
| WO | WO9851812 | 11/1998 |
| WO | WO0011188 | 3/2000 |
| WO | WO2002061109 | 8/2002 |
| WO | WO08006832 | 1/2008 |
| WO | WO2010079594 | 6/2012 |

OTHER PUBLICATIONS

Bleif et al, "A new Bacillus megaterium whole-cell catalyst for the hydroxylation of the pentacyclic triterpene 11-keto-ß-boswellic acid (KBA) based on a recombinant cytochrome P450 system," Applied Microbiology and Biotechnology, Springer, Berlin, DE, vol. 93, No. 3, Jul. 22, 2011, pp. 1135-1146.
Singh et al., "Bacillus subtilis as potential producer for polyhydroxyalkanoates," Microbial Cell Factories 2009, vol. 3, 2009, p. 38.
Desetty et al., "Isolation and heterologous expression of PHA synthesising genes from Bacillus thuringiensis R1," World Journal of Microbiology and Biotechnology, Kluwer Academic Publishers, DO, vol. 24, No. 9, Feb. 2, 2008, pp. 1769-1774.
International Search Report and Written Opinion dated Jan. 20, 2015 for PCT/EP2014/062749 filed Jun. 17, 2014.
Barg et al., "Protein and vitamin production in Bacillus megaterium," In: J. L. Barredo (Eds). Microbial Processes and Products. Humana Press Inc., Totowa, 165-184 (2005).
Bernhardt, "Cytochrome P450: structure, function, and generation of reactive oxygen species," Rev Physiol Biochem Pharmacol. 127:137-221 (1996).
Bernhardt, "Cytochromes P450 as versatile biocatalysts," J Biotechnol. 124(1):128-45 (Jun. 2006).
Ewen et al., "The endogenous adrenodoxin reductase-like flavoprotein arh1 supports heterologous cytochrome P450-dependent substrate conversions in Schizosaccharomyces pombe," FEMS Yeast Res. 8(3):432-41 (May 2008).
Liebergesell, "Purification and characterization of the poly(hydroxyalkanoic acid) synthase from Chromatium vinosum and localization of the enzyme at the surface of poly(hydroxyalkanoic acid) granules," Eur J Biochem. 226 (1):71-80 (Nov. 1994).
Maurer et al., "Immobilisation of P450 BM-3 and an NADP+ Cofactor Recycling System: Towards a Technical Application of Heme-Containing Monooxygenases in Fine Chemical Synthesis," Adv Synth Catal. 345:802-10 (2003).
Nguyen et al., "Metabolism of vitamin d2 to 17,20,24-trihydroxyvitamin d2 by cytochrome p450scc (CYP11A1)," Drug Metab Dispos. 37(4):761-7 (Apr. 2009).
Ostle & Holt, "Nile blue A as a fluorescent stain for poly-beta-hydroxybutyrate," Appl Environ Microbiol. 44 (1):238-41 (Jul. 1982).
Sheu et al., "Rapid detection of polyhydroxyalkanoate-accumulating bacteria isolated from the environment by colony PCR," Microbiology 146:2019-25 (2000).

(Continued)

*Primary Examiner* — Rebecca E Prouty
(74) *Attorney, Agent, or Firm* — McDonell Boehnen Hulbert & Berghoff LLP

(57) ABSTRACT

The subject of the present invention is a whole-cell catalysis process for converting substrates of cytochrome P450 monooxygenases of eukaryotic origin into valuable biotechnological products. The subject of the present invention is also microorganisms genetically engineered to achieve those biotransformations with high rates and processes to prepare these microorganism strains.

12 Claims, 9 Drawing Sheets

Specification includes a Sequence Listing.

(56) References Cited

OTHER PUBLICATIONS

Slominski et al., "Enzymatic metabolism of ergosterol by cytochrome p450scc to biologically active 17alpha,24-dihydroxyergosterol," Chem Biol. 12(8):931-9 (Aug. 2005).
Spiekermann et al., "A sensitive, viable-colony staining method using Nile red for direct screening of bacteria that accumulate polyhydroxyalkanoic acids and other lipid storage compounds," Arch Microbiol. 171(2):73-80 (Jan. 1999).
Stammen et al., "High-yield intra- and extracellular protein production using Bacillus megaterium," Appl Environ Microbiol. 76(12):4037-46 (Jun. 2010).
Steinbuchel & Valentin, "Diversity of bacterial polyhydroxyalkanoic acids," FEMS Microbiol Lett. 128:219-28 (1995).
Stubbe & Tian, "Polyhydroxyalkanoate (PHA) homeostasis: The role of PHA synthase," Nat Prod Rep. 20(5):445-57 (Oct. 2003).
Sudest & Doi, "Synthesis, structure, and properties of polyhydroxyalkanoates: Biological polyester," Prog Polym Sci. 25:1503-1555 (2000).
Szczebara et al., "Total biosynthesis of hydrocortisone from a simple carbon source in yeast," Nat Biotechnol. 21 (2):143-9 (Feb. 2003).
Tuckey et al., "Human cytochrome P450scc (CYP11A1) catalyzes epoxide formation with ergosterol," Drug Metab Dispos. 40(3):436-44 (Mar. 2012).
Tuckey et al., "Kinetics of vitamin D3 metabolism by cytochrome P450scc (CYP11A1) in phospholipid vesicles and cyclodextrin," Int J Biochem Cell Biol. 40(11):2619-26 (2008).
Tuckey et al., "Production of 22-hydroxy metabolites of vitamin d3 by cytochrome p450scc (CYP11A1) and analysis of their biological activities on skin cells," Drug Metab Dispos. 39(9):1577-88 (Sep. 2011).
Tuckey & Cameron, Side-chain specificities of human and bovine cytochromes P-450scc. Eur J Biochem. 217 (1):209-15 (Oct. 1993).
Urlacher & Girhard, "Cytochrome P450 monooxygenases: an update on perspectives for synthetic application," Trends Biotechnol. 30(1):26-36 (Jan. 2012).
Van Bogaert et al., "The role of cytochrome monooxygenases in microbial fatty acid metabolism," FEBS J., 278 (2):206-21 (Jan. 2011).
Wang & Lee, "Production of poly(3-hydroxybutyrate) by fed-batch culture of filamentation-suppressed recombinant *Escherichia coli*," Appl Environ Microbiol. 63(12):4765-9 (Dec. 1997).
Wittchen & Meinhardt, "Inactivation of the major extracellular protease from Bacillus megaterium DSM319 by gene replacement," Appl Microbiol Biotechnol. 42(6):871-7 (Mar. 1995).
Zhou et al., 'Production of alpha-Cyclodextrin Glycosyltransferase in Bacillus megaterium MS941 by systematic codon usage optimization. J Agric Food Chem. 60(41):10285-92 (Oct. 2012).
Nelson, "The cytochrome P450 Homepage," Human Genomics 4:59-65 (Oct. 2009).
Nelson, "Cytochrome P450 Homepage," <http://dmelson.uthsc.edu/cytochromeP450.html>, visited Mar. 14, 2016, pp. 1-15.
English translation of STEINBUECHEL, "Microbial polyester," <http://mibi1.unimuenster.de/Biologie.IMMB.Steinbuechel/Forschung/PHA.html>, visited Mar. 14, 2016, pp. 1-25.
Modern Microbial Ecology, Zhenming Chi et al. eds., Jan. 31, 2010, pp. 379-380.
Up-date Food-Processing, Cheng Lie et al. eds., Dec. 31, 1998, pp. 492-495.
Natural Pharmaceutical Chemistry, Lijun Wu et al. eds., Jun. 30, 2011, pp. 315-318.
McCool et al., "Polyhydroxyalkanoate Inclusion Body-Associated Proteins and Coding Region in Bacillus megaterium," J. Bacteriol. 181 (2) 585-592 (1999).
McCool et al., "PhaC and PhaR are required for polyhydroxyalkanoic acid synthase activity in Bacillus megaterium," J Bacteriol. 183(14):4235-43 (2001).
Sheu et al. , "Rapid detection of polyhydroxyalkanoate-accumulating bacteria isolated from the environment by colony PCR," Microbiology 146 ( Pt 8):2019-25 (2000).

WHOLE-CELL SYSTEM FOR CYTOCHROME P450 MONOOXYGENASES BIOCATALYSIS

This application is a national stage application under 35 U.S.C. § 371 of International Application No. PCT/EP2014/062749, filed Jun. 17, 2014, which claims the benefit of European Patent Application No. EP 13305814.9, filed Jun. 17, 2013, the disclosures of each of which are explicitly incorporated by reference herein.

The subject of the present invention is a whole-cell catalysis process for converting substrates of cytochrome P450 monooxygenases of eukaryotic origin into valuable biotechnological products. The subject of the present invention is also microorganisms genetically engineered to achieve those biotransformations with high rates and processes to prepare these microorganism strains.

BACKGROUND OF THE INVENTION

Cytochrome P450 monooxygenases (P450s) play an important role in the metabolism of a variety of hydrophobic compounds. They are involved in the synthesis of steroids, fatty acids, vitamins, and other biological processes like the detoxification of xenobiotics (Maurer et al, 2003; Urlacher et Girhard, 2012). P450s catalyze a wide variety of reactions including hydroxylations, N-oxidations, N-, O- and S-dealkylations, sulfoxidations, deaminations, desulfurations, dehalogenations, peroxidations, N-oxide reductions, rearrangement reactions, C—C and C—O phenol couplings, cleavage of C—C bonds and others (Bernhardt et al, 1996; Bernhardt et al, 2006;).

The ability of P450s to catalyze the regio-, chemo- and stereospecific oxidation of a vast number of substrates reflects their biological roles and makes them important candidates for biotechnological applications.

Particularly, steroid hormones are widely used as antiinflammatory, contraceptive and antiproliferative drugs. In mammals, the synthesis of these steroids starts with the side-chain cleaving reaction of cholesterol to pregnenolone. Pregnenolone serves as a basis for the production of further steroid hormones such as hydrocortisone (Szczebara et al, 2003) and great interests are associated with its industrial large scale conversion from low-priced substrates such as cholesterol and its plant-derived analogs.

However, side-chain cleaving reaction of cholesterol to pregnenolone is a limiting step in steroids overall process. In mammals, it is catalyzed by a membrane-bound CYP11A1 enzyme using adrenodoxin and adrenodoxin reductase as electron carriers.

Great efforts have been spent in order to reconstitute a sterol side-chain cleaving enzyme system in recombinant microorganisms such as *Escherichia coli* (Sakamoto et al., EP2386634) but it remains difficult to obtain a satisfactory level of enzymatic activity mainly because of the fact that CYP11A1 of mammalian origin is an insoluble membrane-associated enzyme and that CYP11A1 does not seem to properly fold in prokaryotic hosts.

A plasmidless derivative of *B. megaterium* DSM319 has proven to be a valuable host for co-expressing the prokaryotic cytochrome P450 CYP106A2 from *B. megaterium* ATCC 13368 with bovine adrenodoxin reductase (AdR), and adrenodoxin (Adx); it has been applied for the whole-cell conversion of hydrophobic acids with terpene structure such as the antiinflammatory pentacyclic triterpene 11-Keto-β-boswellic acid (KBA). In this work, the recombinant *B. megaterium* system was investigated in comparison with the naturally CYP106A2-expressing *B. megaterium* strain ATCC 13368 and an *E. coli* whole-cell system. The prokaryotic cytochrome P450 CYP106A2 from *B. megaterium* ATCC 13368 is one of only a few cloned bacterial steroid hydroxylases. It was recently identified as the first reported bacterial P450 diterpene hydroxylase, which is able to carry out a one-step regioselective allylitic hydroxylation of abietic acid (Bleif et al 2012).

However, a microorganism which allows, as a whole-cell catalyst, to express and catalyze at high rates the bioconversion of substrates from cytochrome P450 monooxygenases of eukaryotic origin, such as the side-chain cleaving reaction of cholesterol to pregnenolone by insoluble CYP11A1, is still needed.

SUMMARY OF THE INVENTION

Surprisingly, the inventors have found that it was possible to express and catalyze the bioconversion of substrates from cytochrome P450 monooxygenases of eukaryotic origin at high rates, by using a microorganism as a whole-cell catalyst and by increasing its storage capacity dependent of polyhydroxyalkanoate granules.

Especially, the inventors achieved a high rate conversion of cholesterol, cholesterol analogs and derivatives into pregnenolone, hydroxylated cholesterol analogs and secosteroids, by co-expressing into *B. megaterium* MS941 the insoluble CYP11A1 of bovine origin, bovine adrenodoxin reductase (AdR), and bovine adrenodoxin (Adx).

Therefore, a first aspect of the present invention is a genetically engineered microorganism capable of converting cholesterol, cholesterol analogs and derivatives thereof into steroid hormones precursors or derivatives wherein said microorganism comprises at least one DNA sequence encoding a cytochrome P450 of eukaryotic origin, an exogenous DNA sequence encoding Adx and an exogenous DNA sequence encoding AdR.

A second aspect of the present invention is a method for producing steroid hormones precursors, comprising the steps of:
  Providing a microorganism as described above,
  Culturing said microorganism under conditions allowing the expression of exogenous DNA sequences,
  Contacting said microorganism culture with a substrate selected from the group consisting of cholesterol, cholesterol analogs and derivatives, and
  Recovering steroid hormones precursors or derivatives.

A third aspect of the present invention is a method of preparing recombinant strains which are improved with respect to the conversion of cholesterol, cholesterol analogs and derivatives into steroid hormones precursors or derivatives, comprising the steps of:
  Providing a microorganism,
  Introducing by means of genetic engineering techniques into said microorganism at least one DNA sequence encoding a cytochrome P450 of eukaryotic origin, an exogenous DNA sequence encoding Adx, and an exogenous DNA sequence encoding AdR.

A fourth aspect of the present invention is a method for increasing the storage capacity of a microorganism for hydrophobic or hydrophilic compounds comprising the steps of:
  Providing a microorganism comprising a functional endogenous polymerase system capable of building polyhydroxyalkanoate bodies (PHA-bodies); and Modulating by means of genetic engineering techniques into said microorganism, the expression of at least one gene involved in the building of PHA-bodies, thereby obtaining a microorganism with increased storage capacity for hydrophobic or hydrophilic compounds.

These and other features and advantages of the disclosed microorganisms and methods will be more fully understood from the following detailed description taken together with the accompanying claims.

DETAILED DESCRIPTION OF THE INVENTION

1. Genetically Engineered Microorganisms According to the Invention

Surprisingly, the inventors have found that it was possible to express and catalyze the bioconversion of substrates from cytochrome P450 monooxygenases of eukaryotic origin at high rates, by using a microorganism as a whole-cell catalyst.

Especially, the inventors achieved a high rate conversion of cholesterol, cholesterol analogs and derivatives into pregnenolone by co-expressing into B. megaterium MS941 the insoluble CYP11A1 of bovine origin, bovine adrenodoxin reductase (AdR), and adrenodoxin (Adx) as described in example 2 and FIGS. 2-12.

Therefore, the present invention pertains to a genetically engineered microorganism capable of converting cholesterol, cholesterol analogs and derivatives thereof into steroid hormones precursors, wherein said microorganism comprises at least one DNA sequence encoding a cytochrome P450 of eukaryotic origin, an exogenous DNA sequence encoding Adx and an exogenous DNA sequence encoding AdR.

By "genetically engineered" microorganism is meant any microorganism according to the present invention which has been modified by genetic engineering techniques known in the field by the skilled in the art.

Those techniques are conventional techniques, unless otherwise indicated, in the fields of bioinformatics, cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.—in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Those techniques according to the present invention relates to technologies allowing the modulation of gene expression known in the field by the skilled in the art. By "modulation of gene expression" or "modulating one gene by means of genetic engineering techniques" or "genetically engineered microorganism wherein one gene is modulated" are encompassed technologies allowing to overexpress one gene of interest or otherwise to down regulate or to suppress the expression of one gene of interest. By "overexpress" or "down regulate" one gene of interest is meant reaching an expression level of said gene above or under its normal level of expression, respectively. The overexpression of a gene of interest can be achieved as a non-limiting example by introducing into a cell or a microorganism an exogenous DNA sequence encoding for such gene of interest. The down regulation of a gene of interest can be achieved by using gene silencing technologies known by the skilled in the art such as antisense and RNA interference technologies known as gene knockdown technologies. The suppression of a gene can be achieved, as non-limiting example, by a gene replacement experiment of a targeted gene of interest by replacing such gene by a non-functional copy of said gene (as described in example 4 for phaC gene deletion) or by a knock-out experiment deleting one part or all the gene by using specific endonucleases as non-limiting examples.

By "introducing into a cell or a microorganism one DNA sequence by means of genetic engineering techniques" is meant the action of transforming said cell or microorganism with a DNA sequence of interest by any transformation technologies known by the skilled in the art such as a non-limiting example the PEG-mediated protoplast transformation technic used in example 1 (Barg H. et. al (2005).

By "exogenous DNA sequence(s)" is meant nucleic acid sequence(s) non originally and/or naturally express in the considered microorganism or the way it is in the natural strain of microorganism (in term of expression level for example), and which have been used to transform said microorganism in order to obtain a genetically engineered microorganism as referred above. In a specific embodiment, the exogenous DNA sequence originates from another species than the considered microorganism (e.g. another species of microorganism or organism). In another specific embodiment, exogenous sequence originates from the same microorganism.

The term "nucleic acid" will generally refer to at least one molecule or strand of DNA, RNA, or a derivative or mimic thereof, comprising at least one nucleobase, such as, for example, a naturally occurring purine or pyrimidine base found in DNA (e.g., adenine "A," guanine "G," thymine "T," and cytosine "C") or RNA (e.g. A, G, uracil "U," and C). A nucleic acid may be made by any technique known to one of ordinary skill in the art (see above and for example, Sambrook et al. 2000).

In another specific embodiment, said exogenous DNA sequences have been introduced into said microorganism by means of genetic engineering techniques. Any techniques known by the skilled in the art can be used to introduce those sequences such as a non-limiting example the PEG-mediated protoplast transformation technic used in example 1 (Barg H. et. al (2005)).

Said exogenous DNA sequence(s) may encode proteins of interest such as cytochrome P450 and redox partners AdR and Adx and the expression "exogenous DNA" can designate each individual sequence or encompasses a whole sequence comprising each individual sequences. As a non-limiting example, said microorganism has been transformed with one plasmid comprising said exogenous DNA sequences as described in example 1. As another non-limiting example, said exogenous DNA sequences are integrated into the genome of said microorganism by techniques known in the field such as homologous recombination for example.

By "microorganism" is meant the microorganism used to construct said genetically engineered microorganism according to the present invention. In the frame of the present invention, the microorganism can for instance be selected from the list consisting of *Escherichia coli, Bacillus licheniformis, Bacillus megaterium, Bacillus subtilis, Kluyveromyces lactis, Saccharomyces cerevisiae* and *Schizosaccharomyces pombe*.

In a specific embodiment according to the invention, the microorganism is *Bacillus megaterium*. In another specific embodiment according to the invention, the microorganism is a *Bacillus megaterium* strain chosen from the group consisting of strains deposited with Deutsche Stammsammlung von Mikroorganismen und Zellkulturen, hereinafter abbreviated as "DSM", having accession numbers DSM 1517, DSM 1668, DSM 1669, DSM 1670, DSM 1671, DSM 1804, DSM 2894, DSM 30587, DSM 30601, DSM 30782, DSM 30787, DSM 30897, DSM 319, DSM 32, DSM 321, DSM 322, DSM 3228, DSM 333, DSM 337, DSM 339, DSM 344, DSM 3641, DSM 509, DSM 510, DSM 786 and DSM 90 strain.

In a specific embodiment according to the invention, the microorganism is *Bacillus megaterium* DSM 319 strain. In a specific embodiment according to the invention, the microorganism is a *Bacillus megaterium* strain which cannot express the major extracellular protease gene nprM (e.g. a strain of which the major extracellular protease gene nprM is deleted or silenced). In a specific embodiment according to the invention, the microorganism is *Bacillus megaterium* referred to as *Bacillus megaterium* MS941. By *Bacillus megaterium* MS941 strain is meant the strain as referenced in Wittchen K. D. and Meinhardt F., (1995) and in Jingwen Z. and al (2012) and derived from wild-type DSM319 strain by knocking out the major extracellular protease gene nprM.

One aspect of the present invention pertains to a genetically engineered microorganism capable of converting cholesterol, cholesterol analogs and derivatives thereof into steroid hormones precursors or derivatives, wherein said microorganism comprises at least one DNA sequence encoding a cytochrome P450 of eukaryotic origin, an exogenous DNA sequence encoding Adx and an exogenous DNA sequence encoding AdR.

By "cytochrome P450" is meant monooxygenases which are capable of catalyzing numbers of reactions (as reviewed in Van Bogaert, I. N. et al (2011) or in Urlacher V. B. and Girhard M. (2011) or at http://dmelson.uthsc.edu/CytochromeP450.html). Cytochrome P450 of the present invention is membrane-bound (insoluble) or cytoplasmic (soluble) in their respective original hosts.

In a specific embodiment, said cytochrome P450 of the present invention is selected from the group consisting of CYP11A1 (EC: 1.14.15.6 according to the Enzyme Commission number), CYP17A1 (EC: 1.14.99.9 or 4.1.2.30), CYP21A1, CYP11B1 (EC: 1.14.15.4), CYP11B2, CYP3A4, CYP46A1, CYP27A1 and CYP21A2 (EC: 1.14.99.10).

In the frame of the present invention, the cytochrome P450 introduced into the microorganism is of eukaryotic origin, as may be the exogenous AdR and Adx. By the expression "of eukaryotic origin" is meant a protein originally expressed in an (i.e. originating from) eukaryotic organism of the genus *Homo, Rattus, Mus, Sus, Bos, Gallus, Taeniopygia, Ovis, Macacamulatta, Capra, Odontesthes, Trichoplax, Alligator, Eublepharis, Macaca, Papio, Callithrix, Oryctolagus, Mesocricetus, Canis, Rana, Glandirana, Oncorhynchus, Epinephelus, Acanthopagrus, Tautogolabrus, Pimephales, Carassius, Gobiocypris, Anguilla, Dasyatis, Felis* and *Equus* as non-limiting examples, or in cell lines derived from these organisms for in vitro cultures or primary cells taken directly from living tissue and established for in vitro culture. In a specific embodiment, said cytochrome P450 of the present invention is a protein originally expressed in an eukaryotic organism of a species selected from the group consisting of *Homo sapiens, Mus musculus, Rattus norvegicus, Sus scrofa, Bos taurus, Gallus gallus, Taeniopygia guttata, Ovis aries, Taeniopygia guttata, Macaca mulatta, Capra hircus, Equus caballus, Odontesthes bonariensis, Trichoplax adhaerens, Alligator mississippiensis, Eublepharis macularius, Macaca fascicularis, Papio ursinus, Callithrix jacchus, Oryctolagus cuniculus, Mesocricetus auratus, Canis lupus familiaris, Rana catesbeiana, Glandirana rugosa, Oncorhynchus mykiss, Epinephelus coioides, Acanthopagrus schlegelii, Tautogolabrus adspersus, Pimephales promelas, Carassius auratus, Gobiocypris rarus, Anguilla japonica* and *Dasyatis Americana*.

In a specific embodiment, the cytochrome P450 introduced to the microorganism is a cytochrome P450 from Bos Taurus. In another specific embodiment, said cytochrome P450 is CYP11A1 from Bos Taurus (referenced as P00189 in UniProtKB/Swiss-Prot) and catalyzes the side-chain cleavage reaction of cholesterol, cholesterol analogs and derivatives thereof to pregnenolone or other steroid hormones precursors and derivatives as a non-limiting example. In another specific embodiment, said cytochrome P450 catalyzes the hydroxylation of vitamin D2 to 20-hydroxyvitamin D2, 17,20-dihydroxyvitamin D2 and 17,20,24-trihydroxyvitamin D2 (Nguyen M. N. et al. 2009), the hydroxylation of vitamin D3 to 20-hydroxyvitamin D3, 20,23-dihydroxyvitamin D3 and 17,20,23-trihydroxyvitamin D3 (Tuckey R. C. et al. 2008). In another specific embodiment, said cytochrome P450 catalyzes the the oxidation of ergosterol to 17,24-dihydroxyergosterol, 20-hydroxy-22,23-epoxy-22,23-dihydroergosterol and 22-keto-23-hydroxy-22,23-dihydroergosterol (Tuckey R. C. et al. 2012), as other non-limiting examples. In another specific embodiment, the protein sequence of said cytochrome P450 is SEQ ID NO: 2. In another specific embodiment, the protein sequence of said cytochrome P450 is a variant of SEQ ID NO: 2, provided it retains its biological activity. Said microorganism according to the invention comprises at least one DNA sequence encoding a cytochrome P450 of eukaryotic origin or a variant of said cytochrome P450. The encoded cytochrome P450 of eukaryotic origin or the variant thereof according to the invention is not a fusion protein.

By "AdR" is meant Adrenodoxin reductase (EC: 1.18.1.6) or Adrenodoxin-NADP+ reductase, the enzyme which is known as the first component in the mitochondrial Cytochrome P450 electron transfer system and which is involved in the biosynthesis of all steroid hormones.

In a specific embodiment, said AdR enzyme is selected from the group consisting of AR (NADPH:adrenodoxin oxidoreductase (EC=1.18.1.6) encoded by arh1 gene) from *Schizosaccharomyces pombe* or from *Saccharomyces cerevisiae* and FNR (Ferredoxin-NADP reductase (EC=1.18.1.2) encoded by fpr gene) from *Escherichia coli*.

In a specific embodiment, the AdR enzyme which is introduced into the microorganism is AdR from Bos Taurus (referenced as P08165 in UniProtKB/Swiss-Prot). In another specific embodiment, the protein sequence of said AdR is SEQ ID NO: 3. In another specific embodiment, the protein sequence of said AdR is a variant of SEQ ID NO: 3, provided it retains its biological activity.

By "Adx" is meant Adrenodoxin or Ferredoxin 1, the protein which is known for its activity of transferring electrons from Adrenodoxin reductase to CYPA11.

In a specific embodiment, said Adx enzyme is selected from the group consisting of Fdx from mammalian origin, Etp1fd from *Schizosaccharomyces pombe*, Yah1 from *Saccharomyces cerevisiae*.

In a specific embodiment, the Adx enzyme which is introduced into the microorganism is Adx from Bos Taurus as a non-limiting example (referenced as P00257 in UniProtKB/Swiss-Prot). In another specific embodiment, the protein sequence of said Adx is SEQ ID NO: 4. In another specific embodiment, the protein sequence of said Adx is a variant of SEQ ID NO: 4, provided it retains its biological activity.

Said genetically engineered microorganism according to the present invention further comprises a functional endogenous polymerase system capable of building polyhydroxyalkanoate bodies.

By "functional endogenous polymerase system capable of building polyhydroxyalkanoate bodies" is meant a PHA synthase regulon system or an equivalent system with respect to microorganism species which allows said microorganism to produce polyhydroxyalkanoate bodies (PHA-Bodies) or polyhydroxyalkanoate granules or equivalent with respect to considered microorganism species such as polyhydroxybutyrate bodies (PHB-Bodies) or polyhydroxybutyrate granules as non-limiting examples. In a specific embodiment, genetically engineered microorganism according to the present invention is capable of producing polyhydroxyalkanoate bodies (PHA-Bodies) or polyhydroxyalkanoate granules. In another specific embodiment, said genetically engineered microorganism according to the present invention is capable of producing polyhydroxybutyrate bodies (PHB-Bodies) or polyhydroxybutyrate granules.

By PHA synthase regulon system is meant a collection of genes encoding key enzymes of the polyhydroxyalkanoate biosynthesis, which allow the covalent linkage of activated precursors such as (R)-3-hydroxyacyl-coenzyme A thioester with chain length between 3-14 C-atoms, which are substrates of pha-synthase. More than 59 pha-synthase genes with high homology from more than 45 bacterial species have been isolated showing a broad specificity (as described in http://mibi1.unimuenster.de/Biologie.IMMB.Steinbuechel/Forschung/PHA.hta and in Steinbüchel A. and Valentin H. E. 1995, Stubbe J. and Tian J. 2003, Sudesh K. et al. 2000, Liebergesell, M. et al., 1994).

The activity of said polymerase system capable of building polyhydroxyalkanoate bodies according to the present invention can be measured by staining with nile red or nile blue and fluorescence microscopy (As shown in Ostle A. G. and Holt J. G., 1982; Spierkemann P. et al. 1999; Der-Shyan S. et al. 2000) or as mentioned in example 4.

In the expression "functional endogenous polymerase system capable of building polyhydroxyalkanoate bodies" is encompassed the case where the capacity of building polyhydroxyalkanoate bodies is not detectable by regular measurement of activity as mentioned above but where genes of such an endogenous polymerase system are detectable by genomic methods and susceptible to form detectable polyhydroxyalkanoate bodies under particular conditions such as when another pha-synthase gene is overexpressed as a non-limiting example.

In another embodiment, said genetically engineered microorganism according to the present invention further comprises at least one gene involved in the building of PHA-bodies wherein said gene expression is "modulated" as described above. In a specific embodiment, said gene is overexpressed. In another specific embodiment, said gene is down-regulated. In another specific embodiment, said gene is knocked out. In another specific embodiment, said gene is one of the pha-synthase genes as mentioned in the references above. In another specific embodiment, said gene is selected from the group consisting of PhaR (pha synthase), PhaP (Phasin), PhaC (pha synthase), PhaE (Pha synthase), PhaQ (poly-beta-hydroxybutyrate-responsive repressor), PhaB (Acetoacetyl-CoA reductase) and PhaA (3-Ketothiolase). In another specific embodiment, said genetically engineered microorganism according to the present invention comprises overexpressed PhaC (pha synthase). In another specific embodiment, said genetically engineered microorganism according to the present invention comprises overexpressed PhaP (phasin). In another specific embodiment, said genetically engineered microorganism according to the present invention comprises overexpressed PhaA (3-Ketothiolase). In another specific embodiment, said genetically engineered microorganism according to the present invention is knocked out for the Pha depolymerase genes (PhaZ, poly (3-hydroxyalkanoic acid) depolymerase, PhaZ1, PhaZ2 and PhaZ3).

In another embodiment, said genetically engineered microorganism according to the present invention comprises more than one gene involved in the building of PHA-bodies wherein said genes expression are "modulated", such as two, three, four, five, six, seven, eight, nine, ten or more than ten genes.

In another embodiment, said genetically engineered microorganism according to the present invention is modified by overexpressing at least one gene selected in the group consisting of PhaR, PhaP, PhaC, PhaE, PhaB and PhaA and/or down regulating or inactivating at least one gene selected in the group consisting of PhaZ and PhaQ.

In another specific embodiment, said genetically engineered microorganism according to the present invention comprises all together overexpressed PhaA (3-Ketothiolase), PhaB (Acetoacetyl-CoA reductase), PhaC (pha synthase) and PhaR (pha synthase).

In another specific embodiment, said genetically engineered microorganism according to the present invention comprises overexpressed PhaC (pha synthase) and PhaR (pha synthase) as subunits of a same pha polymerase class IV.

In another specific embodiment, said genetically engineered microorganism according to the present invention comprises overexpressed PhaC (pha synthase) and PhaE (pha synthase) as subunits of a same pha polymerase class III.

In another embodiment, said overexpressed genes within genetically engineered microorganism according to the present invention are genes originated from the same microorganism species. In another embodiment, said overexpressed genes within genetically engineered microorganism according to the present invention are genes from other microorganisms species. As non-limiting examples, those genes belong to pha gene system from *Ralstonia eutropha*, *Pseudomonas aeruginosa*, and *Allochromatium vinosum*.

In another specific embodiment, said microorganism of the present invention is *Bacillus megaterium*. In another specific embodiment, said microorganism of the present invention is *Bacillus megaterium* of strain MS941.

Within substrates which the genetically engineered microorganism of the present invention is capable of converting are encompassed phytosterol derived from cycloartenol and lanosterol. Amongst these substrates, by "cholesterol, cholesterol analogs and derivatives thereof" is meant a list of substrates selected from the group consisting of cholesterol, brassicasterol, campesterol, ergostadienol such as ergosta 5, 22 dienol, ergosta 5, 24 (28) dienol, ergosta 5, 24 (25) dienol, ergostatrienol such as ergosta 5, 22, 24 (25) trienol, ergosta 5, 22, 24 (28) trienol, ergosta 5, 7, 22 trienol, ergostatetrenol such as ergosta 5, 7, 22, 24 (25) ou ergosta 5, 7, 22, 24 (28), desmosterol, beta-sitosterol, generol, a mixture of oxysterols, stigmasterol, vitamin D, 7-Dehydrocholesterol and ergosterol as illustrated in examples 3-5 and in FIGS. 2-12. Sterol mixes currently used in industrial processes are also encompassed in this definition of substrates, such as generol 100 and ADM90 (comprising brassicasterol+campesterol+stigmasterol+β-sitosterol at different ratios).

By "variant(s)" is meant protein and nucleic acid variants. Variant proteins may be naturally occurring variants, such as splice variants, alleles and isoforms. Variations in amino acid sequence may be introduced by substitution, deletion or insertion of one or more codons into the nucleic acid sequence encoding the protein that results in a change in the amino acid sequence of the protein. Variant proteins may be a protein having a conservative or non-conservative substitution. For example, a variant of SEQ ID NO: 2, SEQ ID NO: 3 or SEQ ID NO: 4 may be a polypeptide having at least one substitution at a particular amino acid residue. Variant proteins may include proteins that have at least about 80% amino acid sequence identity with a polypeptide sequence disclosed herein. Preferably, a variant protein will have at least about 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a full-length polypeptide sequence or a fragment of a polypeptide sequence as disclosed herein. Amino acid sequence identity is defined as the percentage of amino acid residues in the variant sequence that are identical with the amino acid residues in the reference sequence, after aligning the sequences and introducing gaps, if necessary, to achieve the maximum percent sequence identity, and not considering any conservative substitutions as part of the sequence identity. Sequence identity may be determined over the full length of the variant sequence, the full length of the reference sequence, or both. The percentage of identity for protein sequences may be calculated by performing a pairwise global alignment based on the Needleman-Wunsch alignment algorithm to find the optimum alignment (including gaps) of two sequences along their entire length, for instance using Needle, and using the BLOSUM62 matrix with a gap opening penalty of 10 and a gap extension penalty of 0.5.

Variant nucleic acid sequences may include nucleic acid sequences that have at least about 80% nucleic acid sequence identity with a nucleic acid sequence disclosed herein. Preferably, a variant nucleic acid sequence will have at least about 80%, 81%, 82%, 83%, 84%, 85%, 86%, 87%, 88%, 89%, 90%, 91%, 92%, 93%, 94%, 95%, 96%, 97%, 98%, 99% nucleic acid sequence identity to a full-length nucleic acid sequence or a fragment of a nucleic acid sequence as disclosed herein. Nucleic acid sequence identity can be calculated by methods well-known to one of skill in the art. The percentage of identity may be calculated by performing a pairwise global alignment based on the Needleman-Wunsch alignment algorithm to find the optimum alignment (including gaps) of two sequences along their entire length, for instance using Needle, and using the DNAFULL matrix with a gap opening penalty of 10 and a gap extension penalty of 0.5. Examples of nucleic acid variants can be variants of nucleic acid encoding for proteins of SEQ ID NO: 2, SEQ ID NO: 3 and SEQ ID NO: 4 and variants of nucleic acid encoding pha system genes.

As used herein, "amino acid" refers to the 20 standard alpha-amino acids as well as naturally occurring and synthetic derivatives. A polypeptide may contain L or D amino acids or a combination thereof.

2. Methods of Producing Steroid Hormones According to the Invention

The inventors achieved a high rate conversion of cholesterol, cholesterol analogs and derivatives into pregnenolone, hydroxylated cholesterol analogs and secosteroids, by co-expressing into *B. megaterium* MS941 the insoluble CYP11A1 of bovine origin, bovine adrenodoxin reductase (AdR), and adrenodoxin (Adx) as shown in examples 3-5 and FIGS. 2-12.

Therefore, a second aspect of the present invention pertains to a method for producing steroid hormones precursors and derivatives, comprising the steps of:
  Providing a microorganism as described in the above paragraph entitled "Genetically engineered microorganisms according to the invention",
  Culturing said microorganism under conditions allowing the expression of said exogenous DNA sequences,
  Contacting said microorganism culture with a substrate, and
  Recovering steroid hormones precursors and derivatives.

In a specific embodiment, said "steroid hormones precursors and derivatives" are selected from the group consisting of pregnenolone, 7-Dehydropregnenolone, Hydroxyergosterol, and Hydroxystigmasterol. In another specific embodiment, said steroid hormones precursors and derivatives are selected from the group of hydroxylated cholesterol analogs and secosteroids (such as vitamins D2 and D3 as derivatives of the cholesterol analogs 7-dehydrocholesterol and ergosterol).

By "culturing said microorganism under conditions allowing the expression of said exogenous DNA sequences" is meant any well-known culturing and inducing methods in the biotechnology field. As an illustrative example, culture conditions of a microorganism according to the present invention are given in examples 1 and 2.

By "substrates" which the genetically engineered microorganism of the present invention is able to convert are encompassed phytosterol derivated from cycloartenol and lanosterol.

In a specific embodiment, the present invention pertains to a method for producing steroid hormones precursors and derivatives, comprising the steps of:
  Providing a microorganism as described in the above paragraph entitled "Genetically engineered microorganisms according to the invention",
  Culturing said microorganism under conditions allowing the expression of said exogenous DNA sequences,
  Contacting said microorganism culture with a substrate selected from the group consisting of cholesterol, cholesterol analogs and derivatives, and
  Recovering steroid hormones precursors and derivatives.

By "cholesterol, cholesterol analogs and derivatives thereof" is meant a list of compounds selected from the group consisting of cholesterol, brassicasterol, campesterol, ergostadienol such as ergosta 5, 22 dienol, ergosta 5, 24 (28) dienol, ergosta 5, 24 (25) dienol, ergostatrienol such as ergosta 5, 22, 24 (25) trienol, ergosta 5, 22, 24 (28) trienol, ergosta 5, 7, 22 trienol, ergostatetrenol such as ergosta 5, 7, 22, 24 (25) or ergosta 5, 7, 22, 24 (28), desmosterol, beta-sitosterol, generol, generol 100, sterol ADM90, a mixture of oxysterols, stigmasterol, vitamin D, 7-Dehydrocholesterol and ergosterol as illustrated in examples 3-5 and in FIGS. 2-12.

In a specific embodiment, the present invention pertains to a method for producing steroid hormones precursors and derivatives, comprising the steps of:
  Providing a microorganism as described in the above paragraph entitled "Genetically engineered microorganisms according to the invention",
  Culturing said microorganism under conditions allowing the expression of said exogenous DNA sequences,
  Contacting said microorganism culture with a substrate currently used in industrial processes, and
  Recovering steroid hormones precursors and derivatives.

By "Sterol mixes currently used in industrial processes" are meant substrates, such as generol 100 and ADM90 (comprising brassicasterol+campesterol+stigmasterol+β-sitosterol at different ratios) as illustrated in examples 3-5 and in FIG. 12.

By "contacting" said microorganism culture with a substrate, is meant to make physically interacting said microorganism according to the present invention with a substrate according to the present invention. This interaction can be achieved within a culture medium or not. In a specific embodiment, said culture medium contains agents for the permeabilization of a microorganism according to the present invention and/or the solubilization of a substrate according to the present invention. Dissolution of the substrate in these agents can be prior to the addition to microorganism culture.

These agents can be selected from the group consisting of ethanol, Tween-80, tergitol, polyvinylpyrrolidone (PVP), saponins (such as *Quillaja saponin* which is contained within crude extracts of the soap bark tree *Quillaja saponaria* for example), cyclodextrins and derivatives thereof (e.g. 2-hydroxypropyl-β-cyclodextrin). In another specific embodiment, mixtures of these agents can be used, such as a mixture of ethanol and Tween-80, a mixture of tergitol and ethanol, a mixture of saponins (e.g. *Quillaja saponin*) and cyclodextrins as non-limiting examples. Cyclodextrins derivatives can be used such as 2-hydroxypropyl-β-cyclodextrin as a non-limiting example. In another specific embodiment, substrates are co-crystallized with polyvinylpyrrolidone (PVP).

In another specific embodiment, substrate is first dissolved in 2-hydroxypropyl-β-cyclodextrin prior to the addition to the microorganism culture wherein said culture contains *Quillaja saponin*. In another specific embodiment, substrates are dissolved in a solution comprising a percentage of 2-hydroxypropyl-β-cyclodextrin ranging from 10 to 60%, preferentially 20 to 50%, more preferably 40 to 50% and a percentage of *Quillaja saponin* ranging from 1 to 10%, preferably 2 to 8%, more preferably, 3 to 6%. In another specific embodiment, substrates are dissolved in a solution comprising 45% of 2-hydroxypropyl-β-cyclodextrin and 4% of *Quillaja saponin* as mentioned in example 2.

In another embodiment, final concentration of 2-hydroxypropyl-β-cyclodextrin in the microorganism culture is between 1 and 4%, preferably between 2 and 3%, more preferably 2.25% as illustrated in example 2. In another embodiment, final concentration of *Quillaja saponin* in the microorganism culture is between 0.05 and 0.25%, preferably between 0.075 and 0.225%, more preferably between 0.1 and 0.2% as illustrated in example 2.

In a specific embodiment, the present invention pertains to a method for producing steroid hormones precursors and derivatives, comprising the steps of:
  Providing a microorganism as described in the above paragraph entitled "Genetically engineered microorganisms according to the invention",
  Culturing said microorganism under conditions allowing the expression of said exogenous DNA sequences,
  Contacting said microorganism culture with a substrate, wherein said substrate has been previously dissolved in a solution comprising 2-hydroxypropyl-β-cyclodextrin and *Quillaja saponin*, and
  Recovering steroid hormones precursors and derivatives.

In another specific embodiment, the present invention pertains to a method for producing steroid hormones precursors and derivatives, comprising the steps of:
  Providing a microorganism as described in the above paragraph entitled "Genetically engineered microorganisms according to the invention",
  Culturing said microorganism under conditions allowing the expression of said exogenous DNA sequences,
  Contacting said microorganism culture with a substrate,
    i. wherein said substrate has been previously dissolved in a solution comprising 2-hydroxypropyl-β-cyclodextrin and *Quillaja saponin*,
    ii. wherein final concentrations of these components in the culture medium are respectively 2.25% and 0.2%, and
  Recovering steroid hormones precursors and derivatives.

3. Methods of Preparing Recombinant Strains According to the Invention

A third aspect of the present invention is a method of preparing recombinant strains which are improved with respect to the conversion of substrates such as cholesterol and derived-analogs into steroid hormones precursors as described above, comprising the steps of:
  Providing a microorganism according to the present invention,
  Introducing by means of genetic engineering techniques into said microorganism at least one DNA sequence encoding a cytochrome P450 of eukaryotic origin according to the present invention, an exogenous DNA sequence encoding Adx, and an exogenous DNA sequence encoding AdR.

In a specific embodiment, said method comprises a cytochrome P450 of eukaryotic origin selected from the group consisting of CYP11A1, CYP17A1, CYP11B1, CYP21A1, CYP11B2, CYP3A4, CYP46A1, CYP27A1 and CYP21A2 (EC: 1.14.99.10).

In another specific embodiment, said method includes a microorganism comprising a functional endogenous polymerase system capable of building polyhydroxyalkanoate bodies as described in the above paragraph entitled "Genetically engineered microorganisms according to the invention".

In another specific embodiment, said microorganism of the present method is *Bacillus megaterium*. In another specific embodiment, said microorganism of the present method is *Bacillus megaterium* MS941 strain.

In another embodiment, the method of the present invention further comprises the step of modulating by means of genetic engineering techniques into said microorganism, the expression of at least one gene involved in the building of PHA-bodies as described in the above paragraph entitled "Genetically engineered microorganisms according to the invention".

4. Methods of Increasing the Storage Capacity of a Microorganism According to the Invention Surprisingly, the inventors have now found that it was possible to express and catalyze the bioconversion of substrates from cytochrome P450 monooxygenases of eukaryotic origin at high rates, by using a microorganism as a whole-cell catalyst and by increasing its storage capacity dependent of polyhydroxyalkanoate granules.

Therefore, a fourth aspect of the invention is drawn to a method for increasing the storage capacity of a microorganism for hydrophobic or hydrophilic compounds comprising the steps of:
a. Providing a microorganism comprising a functional endogenous polymerase system capable of building polyhydroxyalkanoate bodies as described in the above paragraphs; and
b. Modulating by means of genetic engineering techniques into said microorganism, the expression of at least one gene involved in the building of PHA-bodies, as described in the above paragraphs,
thereby obtaining a microorganism with increased storage capacity for hydrophobic or hydrophilic compounds.

In a specific embodiment, said hydrophobic compounds are:
(i) cholesterol, cholesterol analogs and derivatives thereof, and/or
(ii) steroid hormones precursors and derivatives thereof.

Therefore, this aspect of the invention is also drawn to a method for increasing the storage capacity of a microorganism for (i) cholesterol, cholesterol analogs and derivatives thereof, and/or (ii) steroid hormones precursors and derivatives thereof comprising the steps of:
a. Providing a microorganism comprising a functional endogenous polymerase system capable of building polyhydroxyalkanoate bodies as described in the above paragraphs; and
b. Modulating by means of genetic engineering techniques into said microorganism, the expression of at least one gene involved in the building of PHA-bodies, as described in the above paragraphs,
thereby obtaining a microorganism with increased storage capacity for (i) cholesterol, cholesterol analogs and derivatives thereof, and/or (ii) steroid hormones precursors and derivatives thereof.

The activity of said polymerase system capable of building polyhydroxyalkanoate bodies according to the present invention can be measured by staining with nile red or nile blue and fluorescence microscopy (Ostle A. G. and Holt J. G., 1982; Spierkemann P. et al. 1999; Der-Shyan S. et al. 2000) and as mentioned in example 4.

In a specific embodiment, said storage capacity is proportionally increased with respect to PhaC polymerase gene expression. In other terms, the introduction of an exogenous DNA sequence encoding a PhaC gene allows to increase the capacity of the microorganism according to the present invention to store Polyhydroxyalkanoates in granules and to increase the capacity of said microorganism to convert substrate into products. As non-limiting example, by overexpressing exogenous phaC gene into Bacillus megaterium MS941 overexpressing CYPA11 and its redox partners, the inventors increased the capacity of said genetically engineered microorganism to convert cholesterol, cholesterol analogs and derivatives into steroid hormones precursors, hydroxylated cholesterol analogs and secosteroids, as described in examples 3 to 5.

In another specific embodiment, said storage capacity is proportionally increased with respect to PhaP gene expression. In other words, the overexpression of an exogenous DNA sequence encoding a PhaP gene allows increasing the capacity of the microorganism according to the present invention to store Polyhydroxyalkanoates in granules and to increase the capacity of said microorganism to convert said substrate into products.

In another specific embodiment, said storage capacity is proportionally increased with respect to PhaA gene expression. In other words, the overexpression of an exogenous DNA sequence encoding a PhaA gene allows to increase the capacity of the microorganism according to the present invention to store Polyhydroxyalkanoates in granules and to increase the capacity of said microorganism to convert said substrate into products.

In another specific embodiment, said storage capacity is proportionally increased with respect to Pha depolymerase genes (PhaZ, poly(3-hydroxyalkanoic acid) depolymerase, PhaZ1, PhaZ2 and PhaZ3) down-regulation. In other words, knock-out of the Pha depolymerase genes (PhaZ, poly(3-hydroxyalkanoic acid) depolymerase, PhaZ1, PhaZ2 and PhaZ3) and suppression or down regulation of the protein(s) encoded by said gene(s) allows to increase the capacity of the microorganism according to the present invention to store Polyhydroxyalkanoates in granules and to increase the capacity of said microorganism to convert said substrate into products.

In another specific embodiment, said storage capacity is proportionally increased with respect to concomitant overexpression of PhaA (3-Ketothiolase), PhaB (Acetoacetyl-CoA reductase), PhaC (pha synthase) and PhaR (pha synthase). In other words, the overexpression of exogenous DNA sequences encoding PhaA, PhaB, PhaC and PhaR genes allows to increase the capacity of the microorganism according to the present invention to store Polyhydroxyalkanoates in granules and to increase the capacity of said microorganism to convert said substrate into products.

In another specific embodiment, said storage capacity is proportionally increased with respect to concomitant overexpression of PhaC (pha synthase) and PhaR (pha synthase) as subunits of a same pha polymerase class IV. In other words, the overexpression of exogenous DNA sequences encoding PhaC and PhaR genes allows to increase the capacity of the microorganism according to the present invention to store Polyhydroxyalkanoates in granules and to increase the capacity of said microorganism to convert said substrate into products.

BRIEF DESCRIPTION OF THE SEQUENCES

SEQ ID NO: 1: Plasmid sequence of pSMF2.1_SCCAA.
SEQ ID NO: 2: Amino acid sequence of CYP11A1.
SEQ ID NO: 3: Amino acid sequence of AdR.
SEQ ID NO: 4: Amino acid sequence of Adx.

EXAMPLES

Example 1: Construction of *B. megaterium* Expression Plasmid pSMF2.1 SCCAA

For the cloning of the respective genes, the following restriction enzymes were used:
CYP11A1: SpeI/MluI
AdR: KpnI/SacI
Adx: BsRGI/SphI Plasmid pSMF2.1_SCCAA is derived from *Bacillus megaterium* shuttle vector pKMBm4 (obtained from the group of Prof. Dr. Dieter Jahn, T U Braunschweig, Stammen S. et al. (2010)). pKMBm4 was modified as as described below:
A) the PacI-restriction site was deleted by mutagenesis,
B) a new multiple cloning site was inserted, (Bleif et al., 2012)
C) fragments encoding adrenodoxin, adrenodoxin reductase and CYP11A1 were inserted.

All three genes are under the control of the strong-inducible promoter PXylA. Each gene contains its own ribosomal binding site.

In *E. coli*, the beta-lactamase is expressed, conferring ampicillin resistance.

In *B. megaterium*, the tetracycline-resistance protein is expressed, conferring tetracycline resistance.

Figure 15:
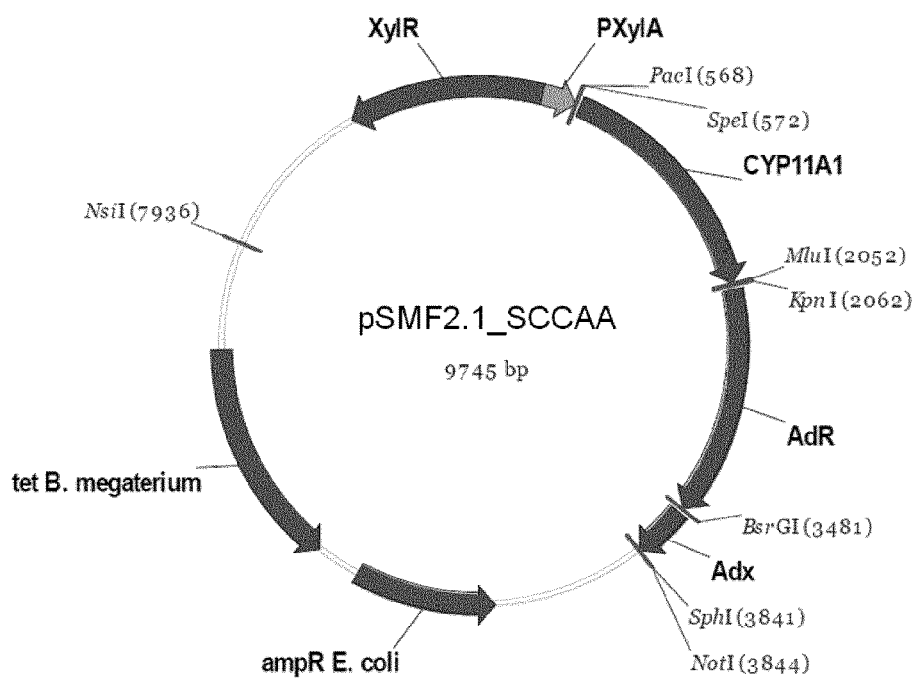
FIG. 15: Map of expression vector pSMF2.1_SCCAA.

Plasmid map and sequence of pSMF2.1_SCCAA are respectively provided in FIG. 15 and SEQ ID N° 1.

*Bacillus megaterium* strain MS941 were obtained from the group of D. Jahn/Technische Universitat Braunschweig (Wittchen K. D. und Meinhardt F., 1995) derived from DSM319/Deutsche Stammsammlung von Mikroorganismen und Zellkulturen.

*B. megaterium* cells were transformed according to the PEG-mediated protoplast transformation by Barg H. et. al (2005).

Example 2: Cultivation Conditions for Recombinant *B. megaterium* and Samples Treatment Either LB-(25 g/L), TB-(24 g/L yeast extract, 12 g/L tryptone, 0.4% glycerol, 10 mM potassium phosphate buffer) or EnPresso™ Tablet medium have been used for the cultivation of *B. megaterium*. All reagents are listed in table 1 below.

Pre-Culture:
Inoculation of 50 mL medium containing 10 μg/mL tetracycline were performed with cells from a plate or glycerol stock.

Main Culture:
Inoculation of 50 mL medium containing 10 μg/mL tetracycline were performed with 500 μL sample of the pre-culture.

Induction of Protein Expression:
The main culture was grown until an optical density of ~0.4 has been reached. Protein expression was induced after addition of 0.25 g xylose dissolved in 1 mL distilled water.

Substrate Solubilization:
Steroids were dissolved in a 45% 2-hydroxypropyl-β-cyclodextrin/4% *Quillaja saponin*-solution. 2.5 ml of the solution were added to the culture directly after protein induction leading to a final *Quillaja saponin* concentration of 0.2% and a final concentration of 2-hydroxypropyl-β-cyclodextrin of 2.25%.

Sample Treatment for HPLC-Analysis:

Steroids without intrinsic absorption were converted into their $\Delta_{4\text{-}3}$-keto-derivatives, to allow photometric detection at 240 nm.

1 mL Culture samples was boiled in water for 1 min. 20 µl cholesterol oxidase-solution (5 mg cholesterol oxidase and 5 mg Na-cholate dissolved in 5 ml 50 mM HEPES buffer pH 7, containing 0.05% Tween-20) was added and the sample was incubated at 37° C. with 1000 rpm shaking for 1 hour. For HPLC analysis, the sample was extracted twice with 1 mL ethylacetate and the extract was dissolved in the appropriate solvent.

TABLE 1

List of reagents

| Reagent | Manufacturer |
| --- | --- |
| 2-Hydroxypropyl-β-cyclodextrin | Sigma-Aldrich (332607) |
| Ampicillin | Roth |
| Cholesterol oxidase (*Nocardia* sp.) | CALBIOCHEM |
| EnPresso tablet medium | Biosilta |
| Ethylacetate | Sigma-Aldrich |
| Glycerol | Grüssing |
| HEPES | Roth |
| $K_2HPO_4$ | Grüssing |
| $KH_2PO_4$ | Grüssing |
| LB | BD |
| Na-cholate | SERVA |
| *Quillaja* saponin | Sigma-Aldrich (S7900) |
| Restriction enzymes | NEB |
| Tetracycline | SERVA |
| Tryptone | BD |
| Tween-20 | Roth |
| Yeast extract | BD |

Example 3: Conversion of Cholesterol, Cholesterol Analogs and Derivatives into Pregnenolone by Genetically Engineered *B. megaterium* MS941 Expressing Bovine CYP11A1 and its Redox Partners Adx and AdR

*Bacillus megaterium* strain MS941 has been genetically modified to express the steroidogenic enzyme CYP11A1 and its redox partners Adx and AdR. *B. megaterium* has been transformed with the expression vector pSMF2.1_SCCAA (FIG. 1) comprising genes for CYP11A1, AdR and Adx under the control of the strongly-inducible promoter PXylA as described in example 1 and encoding respectively for proteins of SEQ ID NO: 2, SEQ ID NO: 3 and SEQ ID NO: 4. So far, the mitochondrial cytochrome P450 CYP11A1 has not been expressed in *Bacillus megaterium*.

Figure 1:
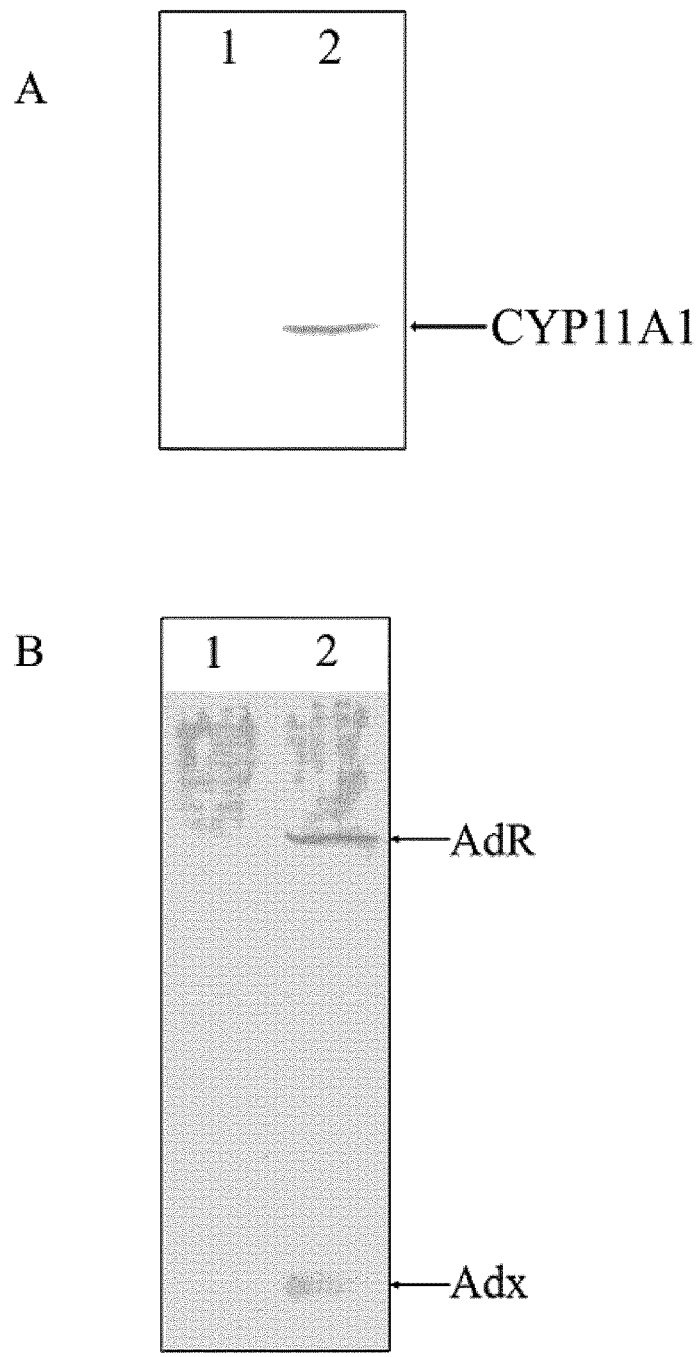
FIG. 1: Immunostainings of CYP11A1 (A) and AdR/Adx (B); Lane 1: wildtype strain of B. megaterium MS941; lane 2: strain of B. megaterium MS941 transformed with pSMF2.1_SCCAA.
Figure 2:
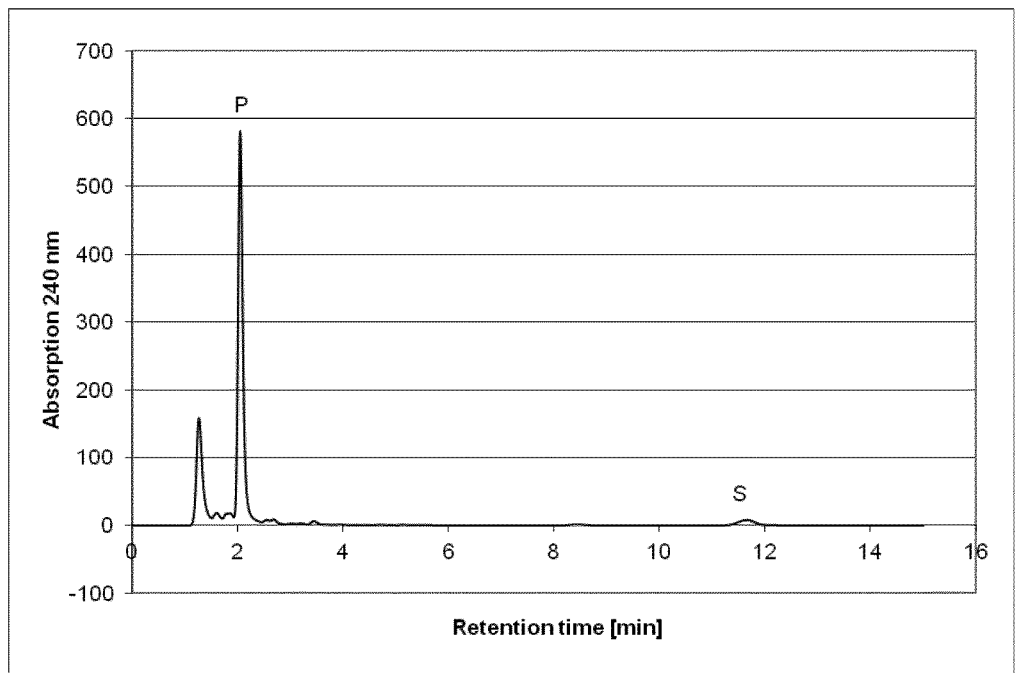
FIG. 2: HPLC chromatogram showing the conversion of cholesterol ("S" for substrate) to pregnenolone ("P" for product) by strain of B. megaterium MS941 transformed with pSMF2.1_SCCAA.
Figure 3:
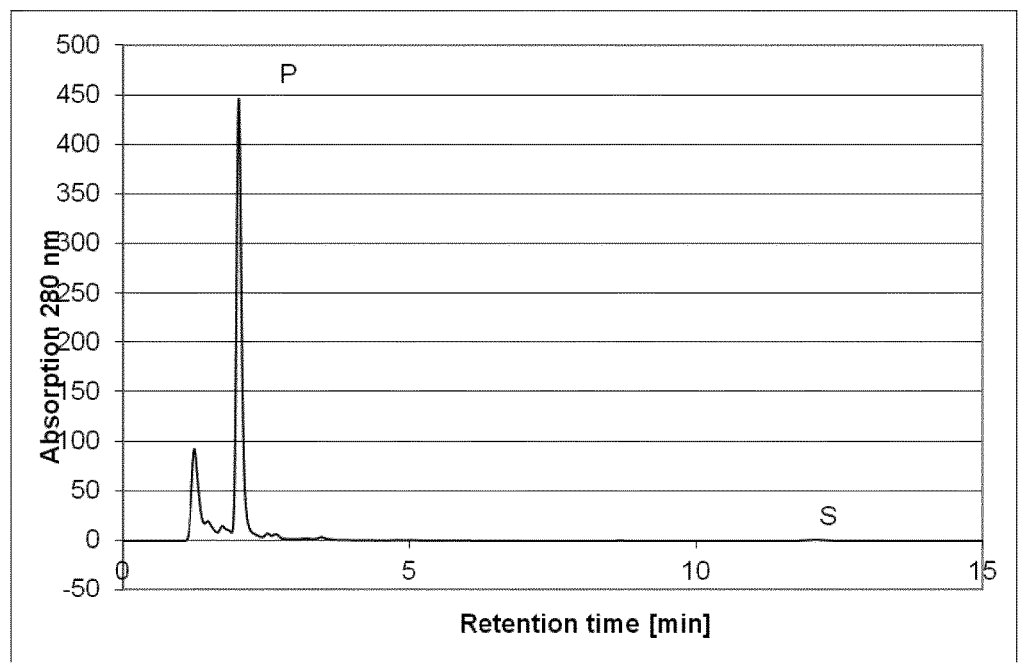
FIG. 3: HPLC chromatogram showing the conversion of 7-dehydrocholesterol ("S" for substrate) to 7-dehydro pregnenolone ("P" for product) by strain of B. megaterium MS941 transformed with pSMF2.1_SCCAA.
Figure 4:
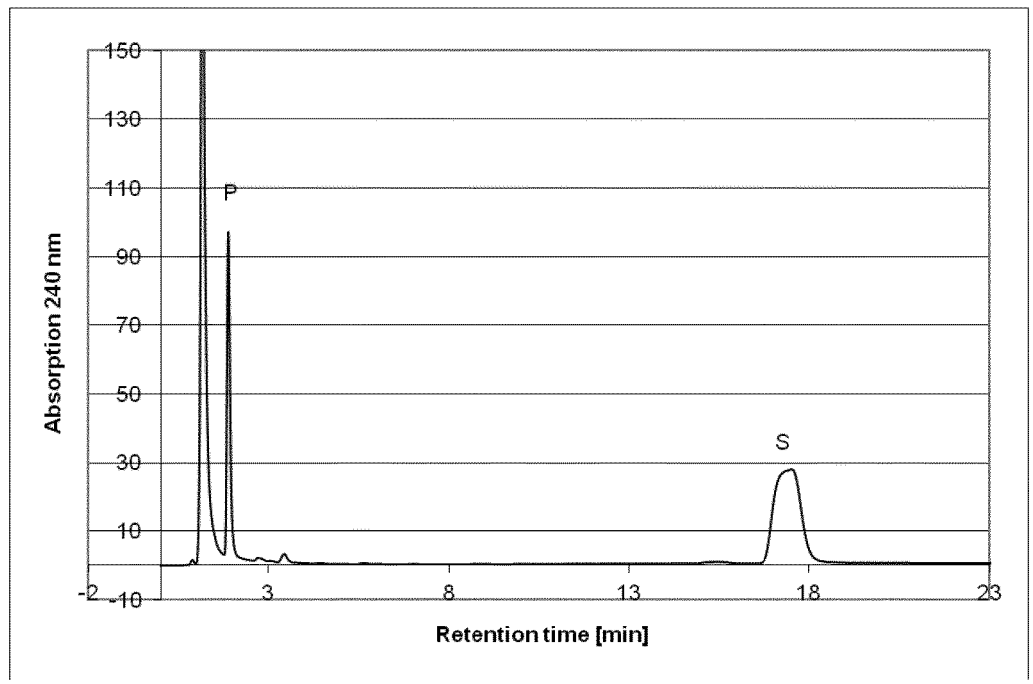
FIG. 4: HPLC chromatogram showing the conversion of campesterol ("S" for substrate) to pregnenolone ("P" for product) by strain of B. megaterium MS941 transformed with pSMF2.1_SCCAA.
Figure 5:
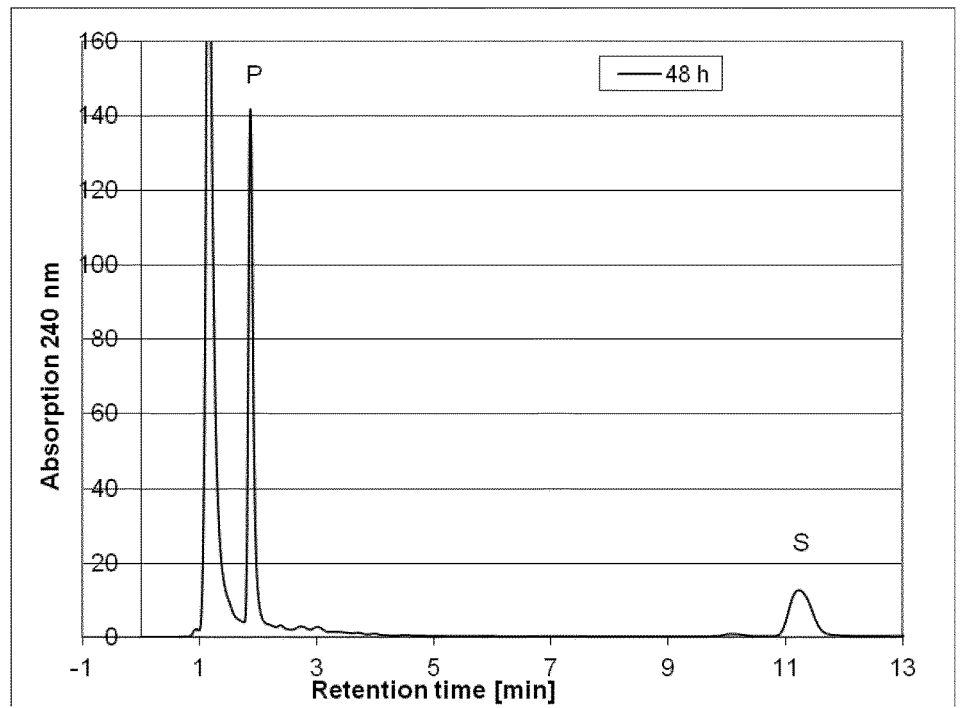
FIG. 5: HPLC chromatogram showing the conversion of ergostadienol ("S" for substrate) to pregnenolone ("P" for product) by strain of *B. megaterium* MS941 transformed with pSMF2.1_SCCAA.
Figure 6:
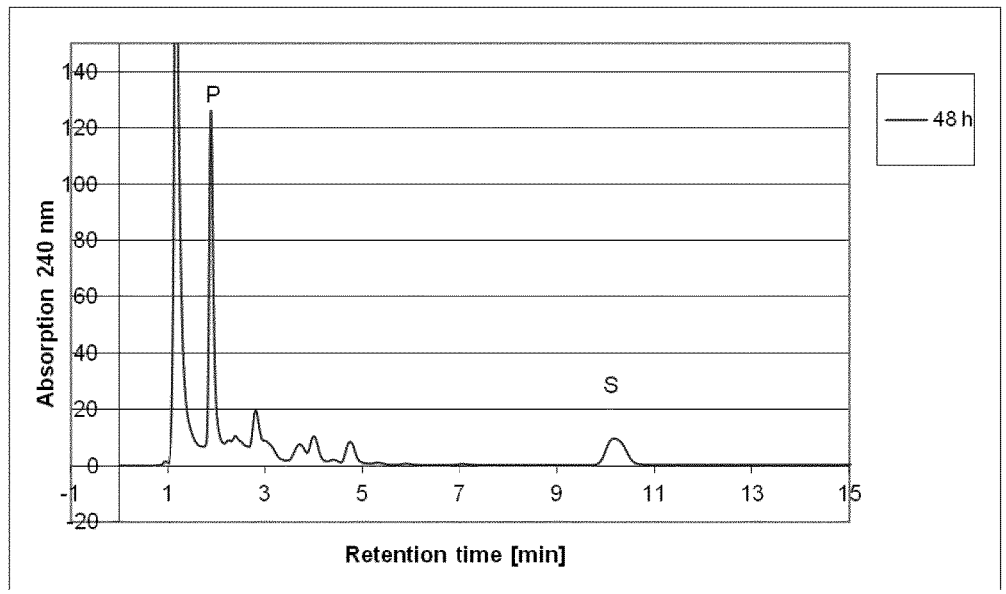
FIG. 6: HPLC chromatogram showing the conversion of desmosterol ("S" for substrate) to pregnenolone ("P" for product) by strain of *B. megaterium* MS941 transformed with pSMF2.1_SCCAA.
Figure 7:
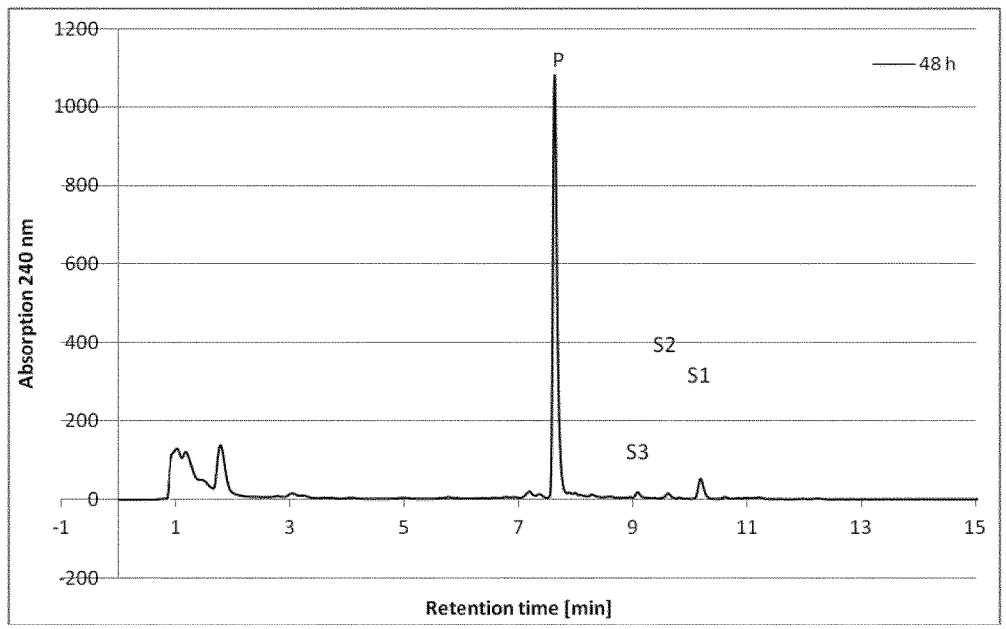
FIG. 7: HPLC chromatogram showing the conversion of mixture of oxysterols ("S1", "S2" and "S3" for the different oxysterol substrates) to pregnenolone ("P" for product) by strain of *B. megaterium* MS941 transformed with pSMF2.1_SCCAA.
Figure 8:
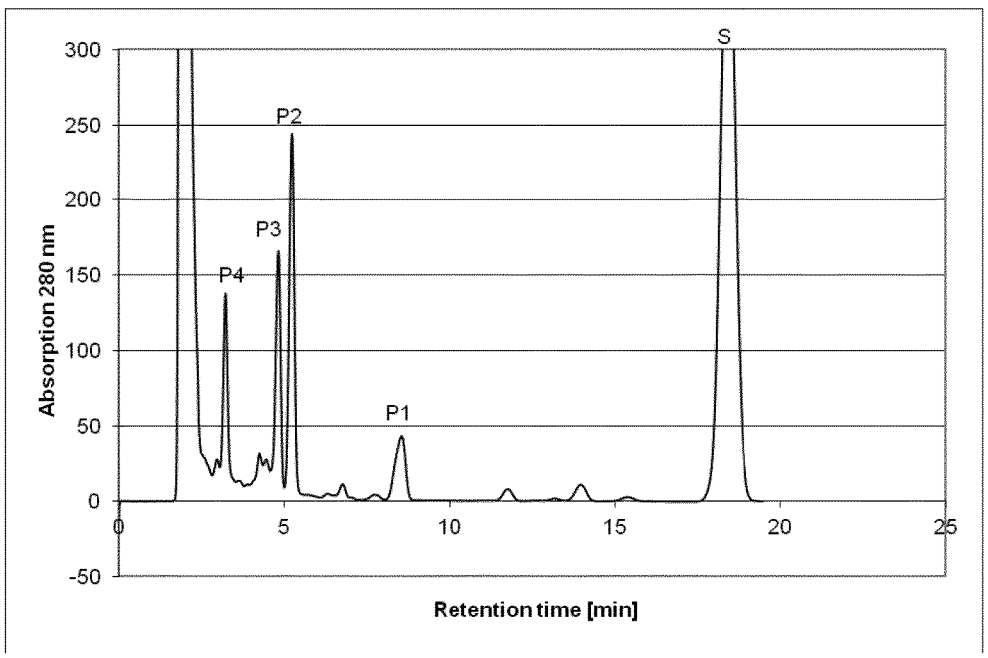
FIG. 8: HPLC chromatogram showing the conversion of ergosterol ("S" for substrate) to hydroxy-ergosterol ("P1", "P2", "P3" and "P4" for the different hydroxylated forms of products) by strain of *B. megaterium* MS941 transformed with pSMF2.1_SCCAA.
Figure 9:
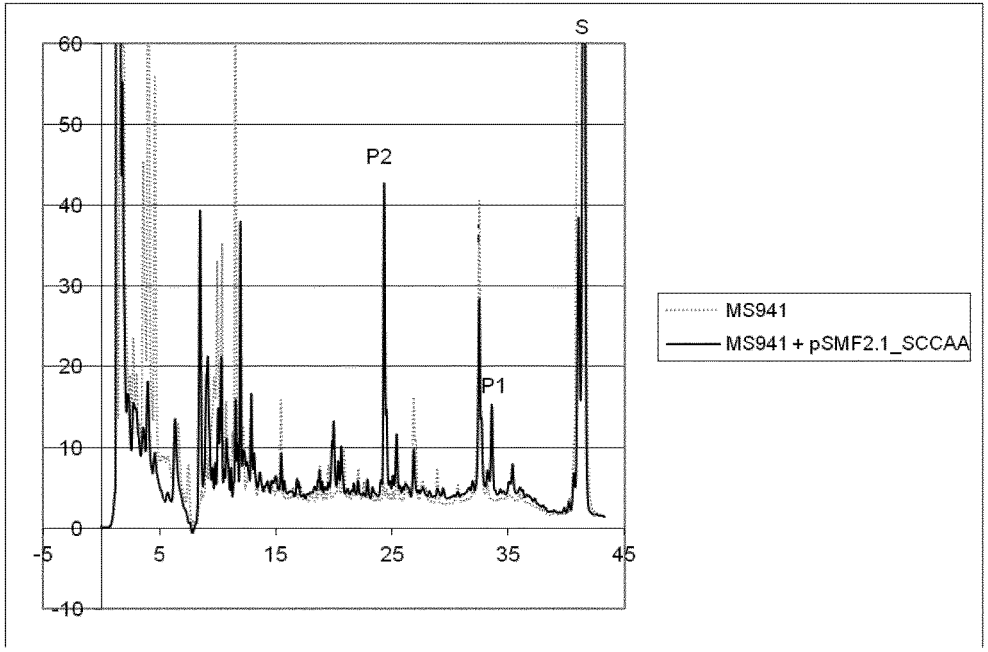
FIG. 9: HPLC chromatogram showing the conversion of vitamin D ("S" for substrate) to hydroxyl-vitamin D ("P1" and "P2" for the different hydroxyl-vitamin D forms) by strain of *B. megaterium* MS941 transformed with pSMF2.1_SCCAA (Solid line) compared to *B. megaterium* MS941 (Dotted line).
Figure 10:
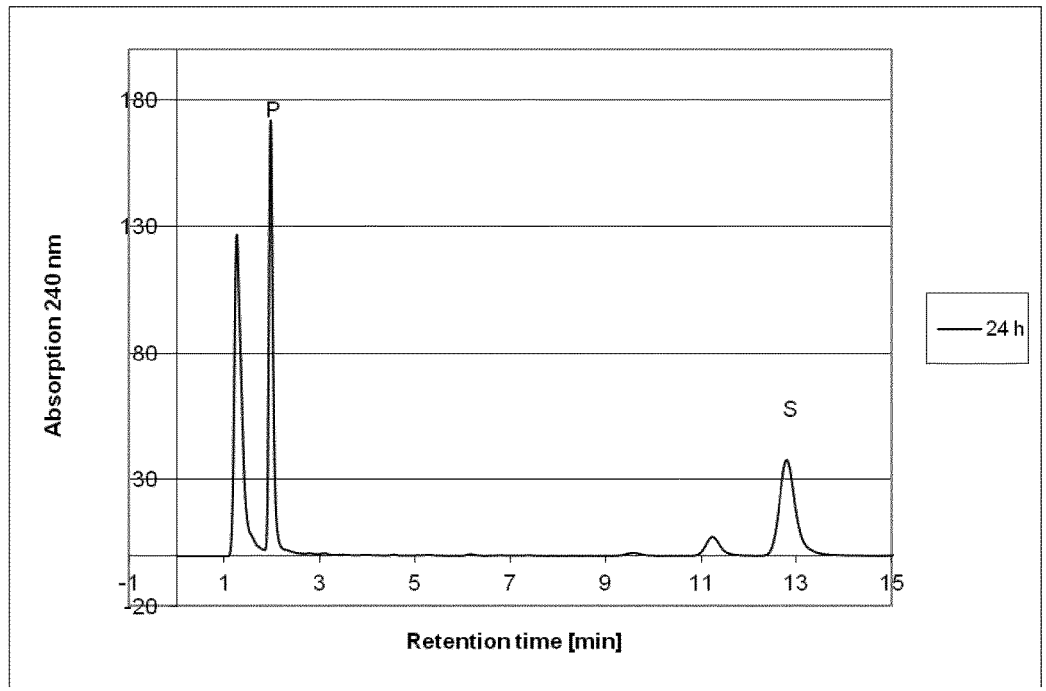
FIG. 10: HPLC chromatogram showing the conversion of beta-sistosterol ("S" for substrate) to pregnenolone ("P" for product) by strain of *B. megaterium* MS941 transformed with pSMF2.1_SCCAA.
Figure 11:
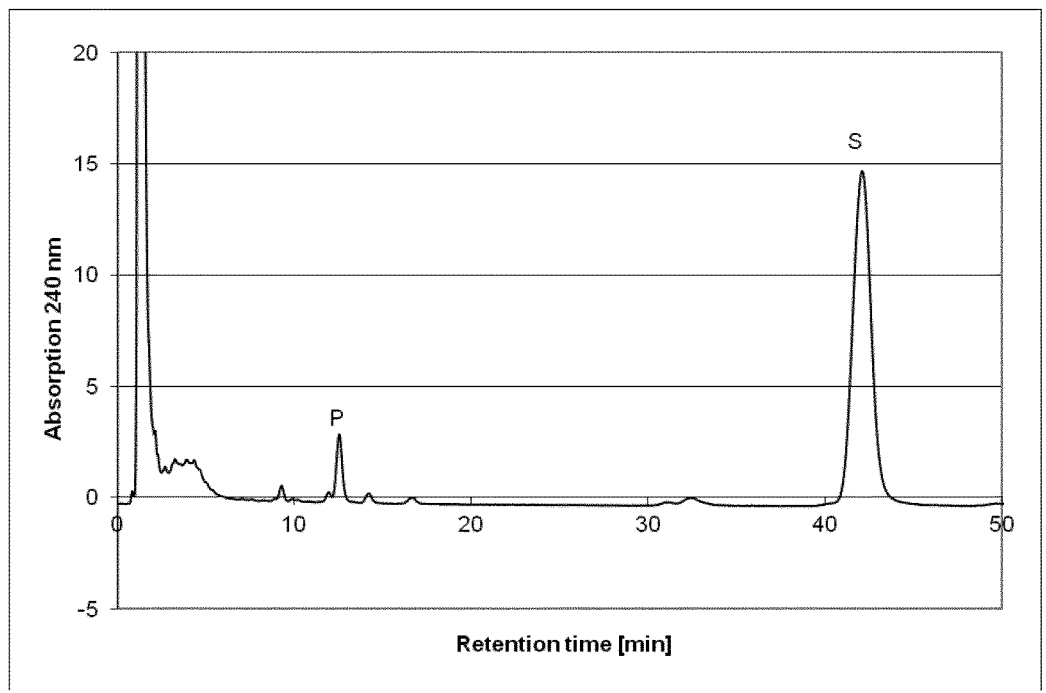
FIG. 11: HPLC chromatogram showing the conversion of stigmasterol ("S" for substrate) to hydroxyl-stigmasterol ("P" for product) by strain of *B. megaterium* MS941 transformed with pSMF2.1_SCCAA.
Figure 12:
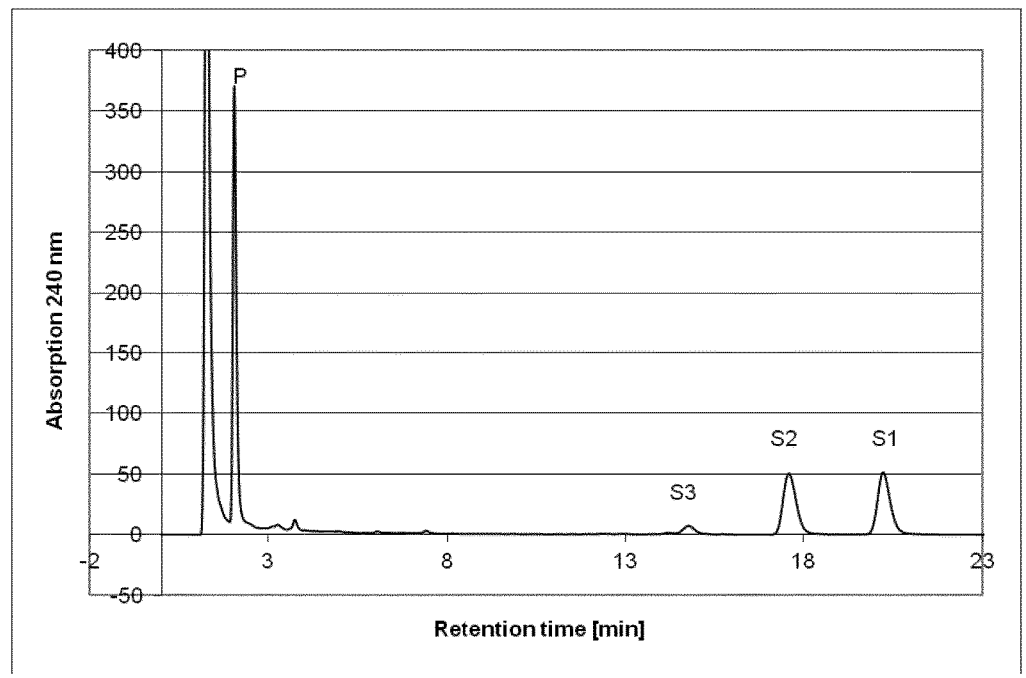
FIG. 12: HPLC chromatogram showing the conversion of generol 100 ("S1", "S2" and "S3" for three of the different sterols contained in general 100) to pregnenolone ("P" for product) by strain of *B. megaterium* MS941 transformed with pSMF2.1_SCCAA.

The expression of all three proteins has been confirmed by immunostaining (FIG. 1).

The following substrates have been solubilized with 2-hydroxypropyl-β-cyclodextrin and *Quillaja* saponin and converted in-vivo with the aforementioned recombinant strain: Cholesterol, 7-Dehydrocholesterol, Campesterol, Ergosta-5,24-dienol, Desmosterol, mixture of oxysterols, Ergosterol, Vitamin D, Beta-Sitosterol, Stigmasterol, Generol. (FIGS. 2-12).

Figure 16:
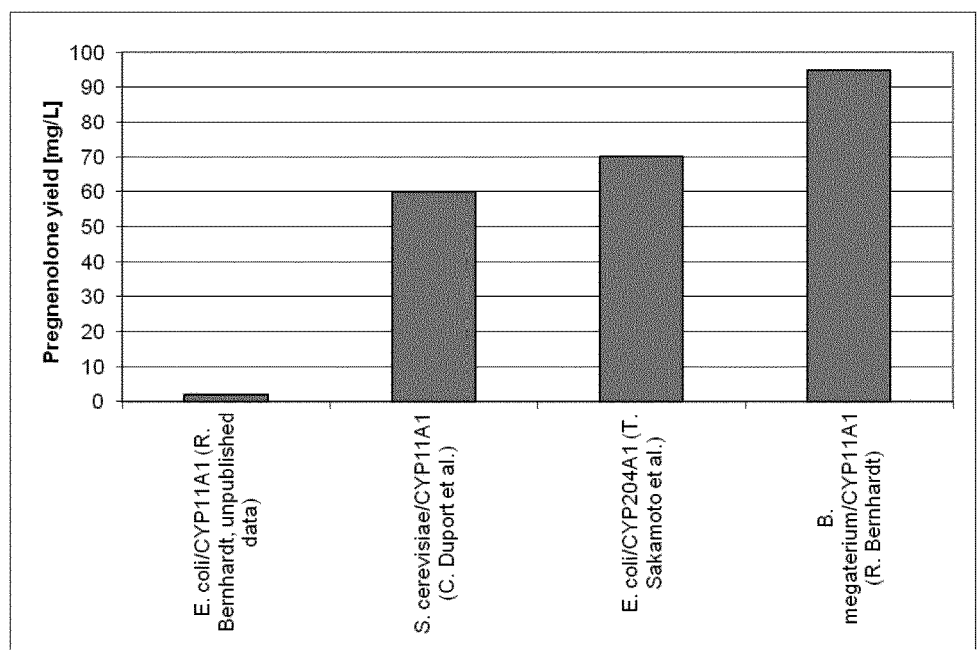
FIG. 16: Comparison of pregnenolone yields produced in different microorganisms expression different cytochrome P450.

As a conclusion, this system allows the whole-cell biocatalysis of the hydrophobic steroids cholesterol, its plant-derived analogs and vitamin D and has the ability to take up high concentrations of highly water-insoluble compounds and convert them at high rates. The product yield of this system is superior to other pregnenolone-producing systems (FIG. 16).

Example 4: Role of Polyhydroxybutyrate-Bodies (PHB-Bodies) into the Conversion of Cholesterol, Cholesterol Analogs and Derivatives into Pregnenolone by Genetically Engineered *B. megaterium* MS941 Expressing Bovine CYP11A1 and its Redox Partners Adx and AdR Fluorescent cholesterol analog 25-NBD cholesterol has been shown to localize to the carbon-storage serving PHB-bodies in living *B. megaterium*-cells (data not shown). In order to localize CYP11A1 in *B. megaterium*-cells, a fusion protein was expressed in living *B. megaterium*-cells consisting of the fluorescent protein eGFP and CYP11A1. Similar to 25-NBD cholesterol, CYP11A1eGFP was localized in the PHB-bodies, whose identity was confirmed by nile red staining (data not shown).

Figure 13:
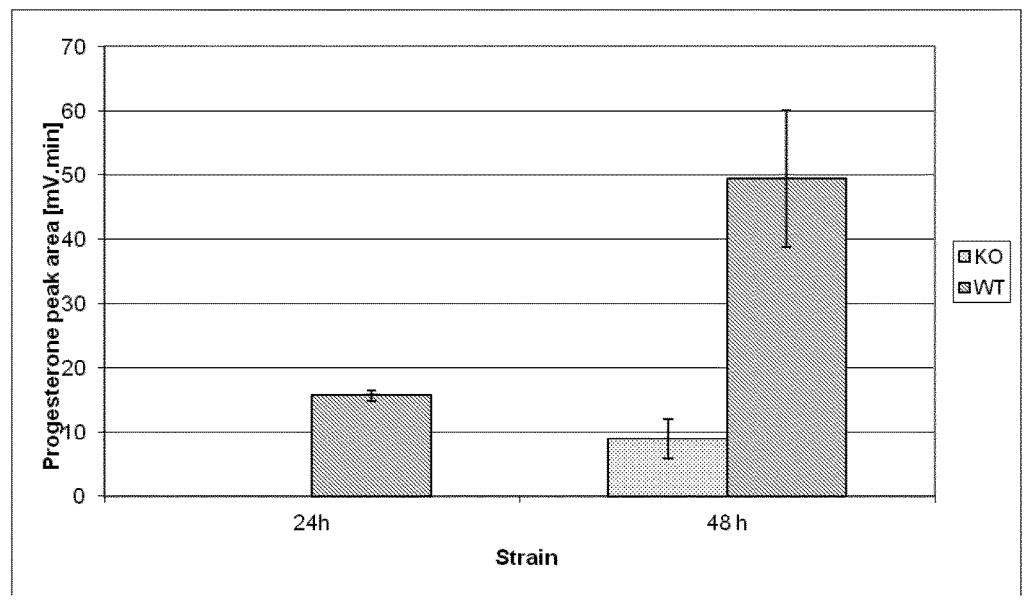
FIG. 13: Comparison of CYP11A1 in vivo activity in absence and presence of polyhydroxybutyrate-bodies (KO: PhaC knockout strain of *B. megaterium* MS941; WT: wild-type of *B. megaterium* MS941 strain) after 24 and 48 hours of reaction.

The PHB-body producing polymerase PhaC has been deleted from the genome of *B. megaterium* by homologous recombination. Briefly, a deletion cassette was constructed, consisting of flanking regions of the PhaC gene. This construct was cloned on a plasmid containing a temperature-sensitive origin of replication. After two homologous recombination events, the curing of the plasmid was achieved by incubation at the non-permissive replication temperature. The deletion of the gene was verified by PCR. In order to verify the role of the PHB-bodies in CYP11A1 aggregation and substrate storage, the resulting absence of PHB-bodies in the *B. megaterium*-cells has been monitored by nile red-staining (data not shown). This morphological change leaded to a drastic decrease in whole-cell conversion activity of the PhaC-knockout strain transformed with pSMF2.1_SCCAA (FIG. 13).

Figure 14:
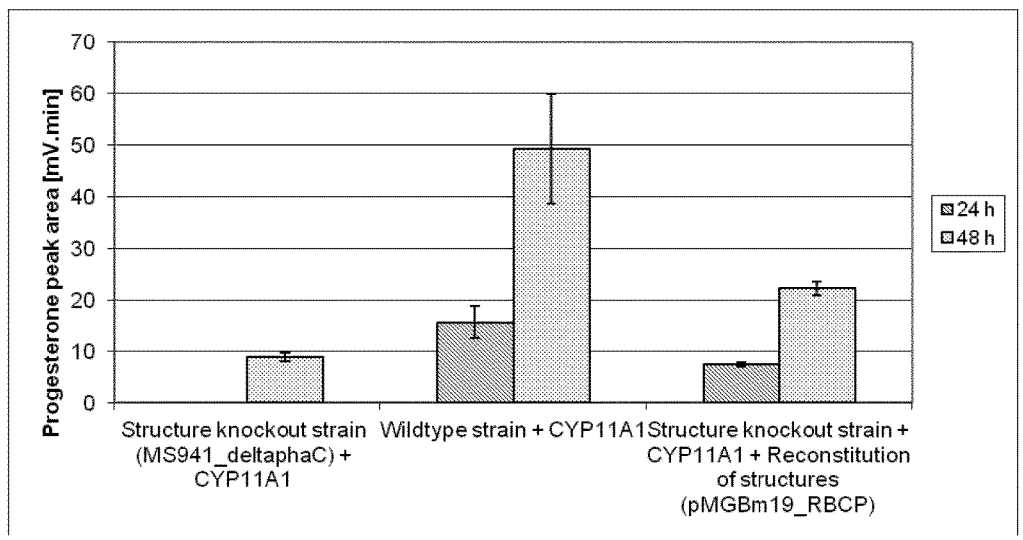
FIG. 14: Restoration of substrate conversion activity in a PHB-depleted strain (MS941_deltaphaC) overexpressing CYP11A1 and its redox partners; comparison of CYP11A1 in vivo activity in absence (Structure Knockout strain (MS941_deltaphaC)+CYP11A1) and presence of polyhydroxybutyrate-bodies (Wildtype strain+CYP11A1) and in a strain wherein PHB-bodies have been reconstituted by transforming the strain with a plasmid encoding the structure operon (Structure Knockout strain(MS941_deltaphaC)+ CYP11A1+reconstitution of structures(pMGBm19_RBCP).

Example 5: Modulation of Polyhydroxybutyrate-Bodies (PHB-Bodies) into a Genetically Engineered *B. megaterium* MS941 Strain Expressing Bovine CYP11A1 and its Redox Partners Adx and AdR a-Conversion of Cholesterol, Cholesterol Analogs and Derivatives into Pregnenolone Substrate conversion activity of the structure-depleted CYP11A1 expressing strain has been restored by transforming it with a plasmid encoding the structure operon encoding for PhaR, PhaB, PhaC and PhaP genes under the control of the original promoter of PhaR, PhaB and PhaC genes (pMGBm19_RBCP plasmid, FIG. 14). The complemented strain exhibited an increase of product yield by more than 100% after 48 hours compared with the structure-depleted strain. The conversion activity was still significantly lower compared with the wildtype strain, since the recombinant expression of the structure operon likely leaded to a reduced expression of CYP11A1 and its redox partners (due to the co-expression of the additional proteins).

These data convincingly illustrates the importance of the granule structures for the whole-cell system.

b-Storage Capacity of *Bacillus megaterium* MS941 by Modulation of Pha System Genes.

The following strategies are applied:

1) Phasin gene (in case of *Bacillus megaterium* phaP) is overexpressed to modify the size of the granules. Phasin gene is inserted into a vector under control of a xylose inducible promoter. *Bacillus megaterium* is transformed with the resulting plasmid. Yield of substrate conversion into product in the strain overexpressing phaP is measured as described in example 2 and in FIGS. 2-12.

2) Pha depolymerase gene is knocked-out to hinder the depolymerization of the granules. Pha depolymerase genome locus is amplified via PCR by introducing a deletion of the locus leading to a nonfunctional gene. This nonfunctional DNA fragment is inserted into a "knock out" vector in order to replace the original genomic functional gene with a nonfunctional one in an gene replacement experiment. Yield of substrate conversion into product in the strain knocked out in the depolymerase gene is measured as described in example 2 and in FIGS. 2-12.

3) *Bacillus megaterium* metabolism is engineered to increase the production of Acetyl-CoA, the main precursor of the metabolism for the granule production, by inserting 3-Ketothiolase gene (phaA) into a vector under control of a xylose inducible promoter. *Bacillus megaterium* is transformed with the resulting plasmid. Yield of substrate conversion into product in the strain overexpressing phaA is measured as described in example 2 and in FIGS. 2-12.

4) Genes involved in granule synthesis (3-Ketothiolase (phaA), Acetoacetyl-CoA reductase (phaB), Phasin (phaP) and pha synthase (phaC/phaR) are overexpressed. The above-mentioned genes are inserted into a vector under control of a xylose inducible promoter. *Bacillus megaterium* is transformed with the resulting plasmid. Yield of substrate conversion into product in the strain overexpressing phaA, phaB, phaP, phaC and phaR is measured as described in example 2 and in FIGS. 2-12.

5) More active pha synthases from other organisms are introduced into *Bacillus megaterium* MS941 strain to produce more polymer. Pha genes, from *Ralstonia eutropha, Pseudomonas aeruginosa* and *Allochromatium vinosum* are used. *Exogenous pha synthases* genes are inserted into a vector under control of a xylose inducible promoter. *Bacillus megaterium* is transformed with the resulting plasmid. Yield of substrate conversion into product in the strain overexpressing pha synthase(s) from other microorganisms is measured as described in example 2 and in FIGS. 2-12.

REFERENCES

Barg H, Malten M, Jahn M and Jahn D. 2005. Protein and vitamin production in *Bacillus megaterium*. In: J. L. Barredo (Eds). Microbial Processes and Products. Humana Press Inc., Totowa, 165-184.

Bernhardt R. 1996. Cytochrome P450: structure, function, and generation of reactive oxygen species. Rev Physiol Biochem Pharmacol. 127:137-221.

Bernhardt R. 2006. Cytochromes P450 as versatile biocatalysts. J Biotechnol. June 25; 124(1):128-45.

Bleif S, Hannemann F, Zapp J, Hartmann D, Jauch J, Bernhardt R. 2012. A new *Bacillus megaterium* whole-cell catalyst for the hydroxylation of the pentacyclic triterpene 11-keto-beta-boswellic acid (KBA) based on a recombinant cytochrome P450 system. Appl Microbiol Biotechnol. 93: 1135-1146

Der-Shvan 51, Yun-Ting W1, Chia-Yin L1. 2000. Rapid detection of polyhydroxyalkanoate-accumulating bacteria isolated from the environment by colony PCR. Microbiology, August 2000, vol. 146, N° 8: 2109-2025.

Ewen K. M., Schiffler B., Uhlmann-Schiffler H., Bernhardt R., Hannemann F. (2008) The endogenous adrenodoxin reductase-like flavoprotein arh1 supports heterologous cytochrome P450-dependent substrate conversions in *Schizosaccharomyces pombe*. FEMS Yeast Res. 8: 432-41

Jingwen Z. Hua L., Guocheng D., Jianghua L. and Jian C. (2012) Production of alpha-Cyclodextrin Glycosyltransferase in *Bacillus megaterium* MS941 by Systematic Codon Usage Optimization. Journal of Agricultural and Food Chemistry 60, 10285-10292.

Liebergesell, M.; Sonomoto, K.; Madkour, M.; Mayer, F.; Steinbuchel, A. 1994. Eur. J. Biochem. 226, 71-80.

Maurer S C, Schulze H, Schmid R D, Urlacher V. 2003. Immobilisation of P450 BM-3 and an NADP$^+$ Cofactor Recycling System: Towards a Technical Application of Heme-Containing Monooxygenases in Fine Chemical Synthesis. Advanced synthesis and catalysis, vol. 345: 802-810

Nguyen M N, Slominski A, Li W, Ng Y R, Tuckey R C. 2009. Metabolism of vitamin d2 to 17,20,24-trihydroxyvitamin d2 by cytochrome p450scc (CYP11A1). Drug Metab Dispos. 2009 April; 37(4):761-7.

Ostle A G and Holt J G. 1982. Appl. Environ. Microbiol. July, vol. 44 no. 1: 238-241

Slominski A, Semak I, Zjawiony J, Wortsman J, Gandy M N, Li J, Zbytek B, Li W, Tuckey R C. 2005. Enzymatic metabolism of ergosterol by cytochrome p450scc to biologically active 17alpha,24-dihydroxyergosterol. 12: 931-939.

Sakamoto, T. 2011. STEROL SIDE CHAIN-CLEAVING ENZYME PROTEIN AND USE THEREOF. European Patent. EP EP 2 386 634 A1

Spiekermann P, Rehm B H, Kalscheuer R, Baumeister D, Steinbuchel A. 1999. A sensitive, viable-colony staining method using Nile red for direct screening of bacteria that accumulate polyhydroxyalkanoic acids and other lipid storage compounds. Arch. Microbiol. January: 171(2): 73-80.

Stammen S, Muller B K, Korneli C, Biedendieck R, Gamer M, Franco-Lara E, Jahn D. 2010. High-yield intra- and extracellular protein production using *Bacillus megaterium*. Appl Environ Microbiol. 76: 4037-4046.

Steinbüchel A, Valentin H E. 1995. Diversity of polyhydroxyalkanoic acids. FEMS Microbiol Lett. 128:219-228.

Stubbe J, Tian J. 2003. Polyhydroxyalkanoate (PHA) homeostasis: The role of PHA synthase. Nat Prod Rep. 20:445-457.

Sudesh K, Abe H, Doi Y. 2000. Synthesis, structure, and properties of polyhydroxyalkanoates: Biological polyesters. Prog Polym Sci. 25:1503-1555.

Szczebara F M, Chandelier C, Villeret C, Masurel A, Bourot S, Duport C, Blanchard S, Groisillier A, Testet E, Costaglioli P, Cauet G, Degryse E, Balbuena D, Winter J, Achstetter T, Spagnoli R, Pompon D, Dumas B. 2003. Nat Biotechnol. 21: 143-149.

Tuckey R C, Cameron K J. 1993. Side-chain specificities of human and bovine cytochromes P-450scc. Eur J Biochem. October 1; 217(1):209-15.

Tuckey R C, Nguyen M N, Slominski A. 2008. Kinetics of vitamin D3 metabolism by cytochrome P450scc (CYP11A1) in phospholipid vesicles and cyclodextrin. Int J Biochem Cell Biol. 40(11) 2008 May 20.

Tuckey R C, Li W, Shehabi H Z, Janjetovic Z, Nguyen M N, Kim T K, Chen J, Howell D E, Benson H A, Sweatman T, Baldisseri D M, Slominski A. 2011. Production of 22-hydroxy metabolites of vitamin d3 by cytochrome p450scc (CYP11A1) and analysis of their biological activities on skin cells. Drug Metab Dispos. 39:1577-1588

Tuckey R C, Nguyen M N, Chen J, Slominski A T, Baldisseri D M, Tieu E W, Zjawiony J K, Li W. 2012. Human cytochrome P450scc (CYP11A1) catalyzes epoxide formation with ergosterol. Drug Metab Dispos. March; 40(3):436-44.

Urlacher V. B. and Girhard M. 2011. Cytochrome P450 monooxygenases: an update on perspectives for synthetic application. Trends in Biotechnology. January 2012; vol 30, N° 1: 26-36.

Van Bogaert, I. N. Groeneboer S, Saerens K, Soetaert W. 2011. The role of cytochrome monooxygenases in microbial fatty acid metabolism. FEBS J., 278 (2), 206-221

The invention claimed is:

1. A genetically engineered microorganism capable of converting cholesterol, cholesterol analogs, and derivatives thereof into steroid hormones precursors,
    wherein said microorganism comprises at least one DNA sequence encoding a cytochrome P450 of eukaryotic origin, an exogenous DNA sequence encoding Adx, and an exogenous DNA sequence encoding AdR,
    wherein said microorganism is *Bacillus megaterium*,
    wherein said cytochrome P450 of eukaryotic origin is selected from the group consisting of CYP11A1, CYP17A1, CYP11B1, CYP11B2, CYP3A4, CYP46A1, CYP27A1, CYP21A1, and CYP21A2, and
    wherein the gene PhaC is overexpressed by introducing into said microorganism an exogenous DNA sequence encoding PhaC.

2. The genetically engineered microorganism according to claim 1, wherein said exogenous DNA sequences have been introduced into said microorganism by means of genetic engineering techniques.

3. The genetically engineered microorganism according to claim 2, wherein said microorganism has been transformed with at least one plasmid comprising said exogenous DNA sequences.

4. The genetically engineered microorganism according to claim 1, wherein said exogenous DNA sequences are integrated into the genome of said microorganism.

5. The genetically engineered microorganism according to claim 1, wherein said microorganism further comprises a functional endogenous polymerase system capable of building polyhydroxyalkanoate bodies.

6. The genetically engineered microorganism according to claim 1, wherein said microorganism is *Bacillus megaterium* MS941 strain.

7. A method for producing steroid hormones precursors, comprising the steps of:
    a. Providing a microorganism according to claim 1,
    b. Culturing said microorganism under conditions allowing the expression of said exogenous DNA sequences,
    c. Contacting said microorganism culture with a substrate selected from the group consisting of cholesterol, cholesterol analogs, and derivatives thereof, and
    d. Recovering steroid hormones precursors.

8. The method according to claim 7, wherein:
    a. said substrate is selected from the group consisting of cholesterol, campesterol, ergostadienol, desmosterol, beta-sitosterol, generol and a mixture of oxysterols, and
    b. said steroid hormones precursor is pregnenolone.

9. The method according to claim 7, wherein said substrate is solubilized into β-cyclodextrin and saponin.

10. A method of preparing a genetically engineered microorganism according to claim 1 capable of converting cholesterol, cholesterol analogs, and derivatives thereof into steroid hormones precursors, comprising the steps of:
    a. Providing a microorganism, wherein said microorganism is *Bacillus megaterium*; and
    b. Introducing by means of genetic engineering techniques into said microorganism at least one DNA sequence encoding a cytochrome P450 of eukaryotic origin, an exogenous DNA sequence encoding Adx, an exogenous DNA sequence encoding AdR, and an exogenous DNA sequence encoding PhaC, to overexpress gene PhaC,
    wherein said cytochrome P450 of eukaryotic origin is selected from the group consisting of CYP11A1, CYP17A1, CYP11B1, CYP11B2, CYP3A4, CYP46A1, CYP27A1, CYP21A1, and CYP21A2.

11. The method according to claim 10, wherein said microorganism comprises a functional endogenous polymerase system capable of building polyhydroxyalkanoate bodies.

12. The method according to claim 10, wherein said microorganism is *Bacillus megaterium* MS941 strain.

* * * * *

SEQUENCE LISTING

```
<160> NUMBER OF SEQ ID NOS: 4

<210> SEQ ID NO 1
<211> LENGTH: 9745
<212> TYPE: DNA
<213> ORGANISM: Artificial Sequence
<220> FEATURE:
<223> OTHER INFORMATION: Plasmid-sequence of pSMF2.1_SCCAA

<400> SEQUENCE: 1
actagcggaa gaactagaca agtcagaagt cttctcgaga ataatatttc cttctaagtc      60
ggttagaatt ccgttaagat agtcgactcc tatatcaata ccaatcgagt agcctgcatt     120
cttattaaaa acaagcatta caggtcttct gccgcctcta gattgccctg ccccaatttc     180
aaaaataaaa tcttttttcaa gcagtgtatt tacttgagag gagacagtag acttgtttaa    240
tcctgtaatc tcagagagag ttgccctgga gacagggag ttcttcaaaa tttcatctaa     300
tattaatttt tgattcattt tttttactaa agcttgatct gcaatttgaa taataaccac     360
tcctttgttt atccaccgaa ctaagttggt gttttttgaa gcttgaatta gatatttaaa     420
agtatcatat ctaatattat aactaaattt tctaaaaaaa acattgaaat aaacattaaa     480
ttaatatatg atggaattgt agttagttta caattccaac aaactaactc aattaagcta     540
gctgatggat aaacttgttc acttaattaa actagtaaat caaggaggtg aatatacaat     600
ggcaagcaca aaaacacctc gcccttattc tgaaattcct agccctggtg ataatggatg     660
gttaaattta tatcattttt ggcgtgaaaa aggtagccaa cgcattcatt ttcgtcatat     720
tgaaaatttt caaaaatatg gacctattta tcgcgaaaaa ttaggaaatt tagaaagcgt     780
atatattatt catcctgaag atgtagctca tttatttaaa tttgaaggat cttatcctga     840
acgctatgat attcctcctt ggcttgctta tcatcgttat tatcaaaaac ctattggcgt     900
attatttaaa aaatctggaa catggaaaaa agatcgtgta gtattaaata cagaagtaat     960
ggctcctgaa gctattaaaa attttattcc gttattaaat cctgtatctc aagattttgt    1020
atctctttta cataaacgta ttaaacaaca aggatctgga aaatttgttg gagacattaa    1080
agaagattta tttcattttg cgtttgaatc tattacaaat gttatgtttg gagaacgcct    1140
tggaatgtta gaagaaacgg taaaccctga agctcaagaa tttattgatg ctgtatataa    1200
aatgtttcat acatctgtac ctttattaaa cgtacctcct gaacttttatc gtcttttcg    1260 aacgaaaacg tggcgtgatc atgtagctgc ttgggataca atttttaata agcggaaaa    1320 atacacggaa attttttatc aagatttacg tcgtaaaaca gaatttcgta attatccggg    1380
aattctttat tgtttactta aaagcgaaaa gatgttatta gaagatgtaa aagctaatat    1440
cacagaaatg ttagcaggtg gagtaaatac aacaagcatg acattacaat ggcatcttta    1500
tgaaatggct cgcagcttaa acgtacaaga aatgttacgt gaagaagtat taaacgctcg    1560
tcgtcaagct gaaggtgata tttctaaaat gttacaaatg gttccattat taaaagcttc    1620
tattaaagaa acgttacgtt tacatccaat tagcgtaacg cttcaacgtt atcctgaatc    1680
tgatttagta ttacaagatt atcttattcc tgctaaaaca ttagtacaag tagctatta    1740 tgctatggga cgtgatcctg ctttttttc ttctcctgat aaatttgatc ctacacgttg    1800
gttatctaaa gataaagatc ttattcattt tcgcaatctt ggatttggat ggggagtacg    1860
```

```
tcaatgtgta ggacgtcgta ttgctgaatt agaaatgacg cttttcttta ttcacattct    1920
tgaaaacttt aaagtggaaa tgcaacatat tggagatgta gacacgattt ttaacttaat    1980
tcttacgcct gataaaccta ttttttagt atttcgtcct tttaatcaag atcctcctca     2040
agcttaataa acgcgtggta ccaaatcaag gaggtgaata tacaatgtct acacaagaac    2100
aaacacctca aatttgtgta gtaggatctg gacctgctgg attttataca gctcaacatc    2160
ttttaaaaca tcattctcgc gctcatgtag atatttatga aaacaacttt gtaccttttg    2220
gattagttcg ttttggagta gctcctgatc atcctgaagt aaaaaacgta attaacacat    2280
ttacacagac agctcgttct gatcgttgtg ctttttatgg aaatgtagaa gtaggacgtg    2340
atgtaacagt acaagaactt caagatgctt atcatgctgt agtattatct tatggtgctg    2400
aagatcatca agctttagat attccaggtg aagaattacc tggtgtattt tctgctcgtg    2460
cttttgtagg atggtataat ggattacctg aaaatcgtga attagctcct gatttatctt    2520
gtgatacagc tgtaatttta ggacaaggca acgtagcttt agatgtagct cgtattttat    2580
taacacctcc ggatcatttta gaaaaacgg atattacaga agctgctctt ggagctttac    2640
gtcaatctcg tgtaaaaaca gtatggattg taggacgtcg tggacccttta caagtagctt    2700 ttacgattaa agaacttcgc gaaatgattc aattacctgg aacacgtcct atgttagatc    2760
ctgctgattt tttaggactt caggatcgta ttaaagaagc tgcacgtcct cgtaaacgtt    2820
taatggaatt attattacgt acagctacag aaaaacctgg tgtagaagaa gctgctcgta    2880
gagcatctgc ttctcgtgct tggggattac gttttttttcg tagccctcaa caagtattac    2940
cttctcctga tggacgtcgt gctgctggaa ttcgtttagc tgtaacacgt ttagaaggta    3000
ttggagaagc tacacgtgct gtacctacag gtgatgtaga agatttaccst tgtggacttg    3060 tattaagctc tattggatat aaatctcgtc ctattgatcc ttctgtaccct tttgatccta    3120 aattaggtgt agtacctaat atggaaggac gtgtagtaga tgtacctgga ttatattgtt    3180
ctggatgggt aaaacgtgga cctacaggtg taattacaac aacaatgaca gatagctttt    3240
taacaggcca aattctttta caagatctta agctggaca tttaccttca ggacctcgtc    3300
ctggatctgc tttattaaaa gctttacttg attctcgtgg agtatggcct gtatcttttt    3360
ctgattggga aaaattagat gctgaagaag tatctagagg acaagcttct ggaaaacctc    3420
gtgaaaaatt attagatcct caagaaatgc ttcgtttact tggccactaa taagagctct    3480
gtacaaatca aggaggtgaa tatacaatgt cttcttctga agataaaata acagtccact    3540
ttataaaccg tgatggtgaa acattaacaa ccaaaggaaa aattggtgac tctctgctag    3600
atgttgtggt tcaaaataat ctagatattg atggttttgg tgcatgtgag gaaaccttgg    3660
cttgttctac ctgtcaccte atctttgaac agcacatatt tgagaaattg gaagcaatca    3720
ctgatgagga gaatgacatg cttgatctgg catatggact aacagataga tcgcggttgg    3780
gctgccagat ctgtttgaca aaggctatgg acaatatgac tgttcgagta ccatagcatg    3840
cgcggccgcc atgccggcta aacctcgcga acggattcac cggtccaaga attggagcta    3900
attaattctt gcggagaact gtgaatgcgc aaaccaaccc ttggcagaac atatccatcg    3960
cgtccgccat ctccagcagc cgcacgcggc gcatctcggg ccgcgttgct ggcgtttttc    4020
cataggctcc gccccctga cgagcatcac aaaaatcgac gctcaagtca gaggtggcga    4080
aacccgacag gactataaag ataccaggcg tttcccctg gaagctccct cgtgcgctct    4140
cctgttccga ccctgccgct taccggatac ctgtccgcct ttctcccttc gggaagcgtg    4200
```

```
gcgctttctc atagctcacg ctgtaggtat ctcagttcgg tgtaggtcgt tcgctccaag   4260
ctgggctgtg tgcacgaacc ccccgttcag cccgaccgct gcgccttatc cggtaactat   4320
cgtcttgagt ccaacccggt aagacacgac ttatcgccac tggcagcagc cactggtaac   4380
aggattagca gagcgaggta tgtaggcggt gctacagagt tcttgaagtg gtggcctaac   4440
tacggctaca ctagaaggac agtatttggt atctgcgctc tgctgaagcc agttaccttc   4500
ggaaaaagag ttggtagctc ttgatccggc aaacaaacca ccgctggtag cggtggtttt   4560
tttgtttgca agcagcagat tacgcgcaga aaaaaggat ctcaagaaga tcctttgatc   4620
ttttctacgg ggtctgacgc tcagtggaac gaaaactcac gttaagggat tttggtcatg   4680
agattatcaa aaaggatctt cacctagatc cttttaaatt aaaaatgaag ttttaaatca   4740
atctaaagta tatatgagta aacttggtct gacagttacc aatgcttaat cagtgaggca   4800
cctatctcag cgatctgtct atttcgttca tccatagttg cctgactccc cgtcgtgtag   4860
ataactacga tacgggaggg cttaccatct ggccccagtg ctgcaatgat accgcgagac   4920
ccacgctcac cggctccaga tttatcagca ataaaccagc cagccggaag ggccgagcgc   4980
agaagtggtc ctgcaacttt atccgcctcc atccagtcta ttaattgttg ccgggaagct   5040
agagtaagta gttcgccagt taatagtttg cgcaacgttg ttgccattgc tgcaggcatc   5100
gtggtgtcac gctcgtcgtt tggtatggct tcattcagct ccggttccca acgatcaagg   5160
cgagttacat gatccccat gttgtgcaaa aaagcggtta gctccttcgg tcctccgatc   5220
gttgtcagaa gtaagttggc cgcagtgtta tcactcatgg ttatggcagc actgcataat   5280
tctcttactg tcatgccatc cgtaagatgc ttttctgtga ctggtgagta ctcaaccaag   5340
tcattctgag aatagtgtat gcggcgaccg agttgctctt gcccggcgtc aacacgggat   5400
aataccgcgc cacatagcag aactttaaaa gtgctcatca ttggaaaacg ttcttcgggg   5460
cgaaaactct caaggatctt accgctgttg agatccagtt cgatgtaacc cactcgtgca   5520
cccaactgat cttcagcatc ttttactttc accagcgttt ctgggtgagc aaaaacagga   5580
aggcaaaatg ccgcaaaaaa gggaataagg gcgacacgga aatgttgaat actcatactc   5640
ttccttttc aatattattg aagcatttat cagggttatt gtctcatgag cggatacata   5700
tttgaatgta tttagaaaaa taaacaaata ggggttccgc gcacatttcc ccgaaaagtg   5760
ccacctgacg tctaagaaac cattattatc atgacattaa cctataaaaa taggcgtatc   5820
acgaggccct ttcgtcttca agaattcctg ttataaaaaa aggatcaatt tgaactctc   5880
tcccaaagtt gatcccttaa cgatttagaa atccctttga gaatgtttat atacattcaa   5940
ggtaaccagc caactaatga caatgattcc tgaaaaaagt aataacaaat tactatacag   6000
ataagttgac tgatcaactt ccataggtaa caacctttga tcaagtaagg gtatggataa   6060
taaaccacct acaattgcaa tacctgttcc ctctgataaa aagctggtaa agttaagcaa   6120
actcattcca gcaccagctt cctgctgttt caagctactt gaaacaattg ttgatataac   6180
tgttttggtg aacgaaagcc cacctaaaac aaatacgatt ataattgtca tgaaccatga   6240
tgttgtttct aaaagaaagg aagcagttaa aaagctaaca gaaagaaatg taactccgat   6300
gtttaacacg tataaggac ctcttctatc aacaagtatc ccaccaatgt agccgaaaat   6360
aatgacactc attgttccag ggaaaataat tacacttccg atttcggcag tacttagctg   6420
gtgaacatct ttcatcatat aaggaaccat agagacaaac cctgctactg ttccaaatat   6480
aattccccca caaagaactc caatcataaa aggtatattt ttccctaatc cgggatcaac   6540
aaaaggatct gttactttcc tgatatgttt tacaaatatc aggaatgaca gcacgctaac   6600
```

```
gataagaaaa gaaatgctat atgatgttgt aaacaacata aaaaatacaa tgcctacaga    6660
cattagtata attcctttga tatcaaaatg acctttatc cttacttctt tctttaataa     6720
tttcataaga aacggaacag tgataattgt tatcatagga atgagtagaa ataggacca     6780 atgaatataa tgggctatca ttccaccaat cgctggaccg actccttctc ccatggctac    6840
tatcgatcca ataagaccaa atgctttacc cctattttcc tttggaatat agcgcgcaac    6900
tacaaccatt acgagtgctg gaaatgcagc tgcaccagcc ccttgaataa aacgagccat    6960
aataagtaag gaaagaaag aatggccaac aaacccaatt accgacccga aacaatttat     7020
tataattcca ataggagta accttttgat gcctaattga tcagatagct ttccatatac     7080
agctgttcca atggaaaagg ttaacataaa ggctgtgttc acccagtttg tactcgcagg    7140
tggtttatta aaatcatttg caatatcagg taatgagacg ttcaaaacca tttcatttaa    7200
tacgctaaaa aaagataaaa tgcaaagcca aattaaaatt tggttgtgtc gtaaattcga    7260
ttgtgaatag gatgtattca catttcaccc tccaataatg agggcagacg tagtttatag    7320
ggttaatgat acgcttccct cttttaattg aaccctgtta cattcattac acttcataat    7380
taattcctcc taaacttgat taaaacattt taccacatat aaactaagtt ttaaattcag    7440
tatttcatca cttatacaac aatatggccc gtttgttgaa ctactcttta ataaaataat    7500
ttttccgttc ccaattccac attgcaataa tagaaaatcc atcttcatcg cttttttcgt    7560
catcatctgt atgaatcaaa tcgccttctt ctgtgtcatc aaggtttaat tttttatgta    7620
tttcttttaa caaaccacca taggagatta acctttacg gtgtaaacct tcctccaaat    7680
cagacaaacg tttcaaattc ttttcttcat catcggtcat aaaatccgta tcctttacag   7740
gatattttgc agtttcgtca attgccgatt gtatatccga tttatattta tttttcggtc   7800
gaatcatttg aactttttaca tttggatcat agtctaattt cattgccttt ttccaaaatt   7860
gaatccattg tttttgattc acgtagtttt ctgtattctt aaaataagtt ggttccacac    7920
ataccaatac atgcatgtgc tgattataag aattatcttt attatttatt gtcacttccg    7980
ttgcacgcat aaaaccaaca agatttttat taattttttt atattgcatc attcggcgaa    8040
atccttgagc catatctgac aaactcttat ttaattcttc gccatcataa acattttta    8100 ctgttaatgt gagaaacaac caacgaactg ttggcttttg tttaataact tcagcaacaa    8160
ccttttgtga ctgaatgcca tgtttcattg ctctcctcca gttgcacatt ggacaaagcc    8220
tggatttaca aaaccacact cgatacaact ttctttcgcc tgtttcacga ttttgtttat    8280
actctaatat ttcagcacaa tcttttactc tttcagcctt tttaaattca agaatatgca   8340
gaagttcaaa gtaatcaaca ttagcgattt tcttttctct ccatggtctc acttttccac   8400
tttttgtctt gtccactaaa acccttgatt tttcatctga ataaatgcta ctattaggac    8460
acataatatt aaaagaaacc cccatctatt tagttatttg tttggtcact tataacttta    8520
acagatgggg ttttttctgtg caaccaattt taagggtttt caatacttta aaacacatac   8580
ataccaacac ttcaacgcac ctttcagcaa ctaaaataaa aatgacgtta tttctatatg    8640
tatcaagata agaagaaca agttcaaaac catcaaaaaa agacaccttt tcaggtgctt     8700
tttttatttt ataaactcat tccctgatct cgacttcgtt cttttttac ctctcggtta     8760 tgagttagtt caaattcgtt cttttaggt tctaaatcgt gttttcttg gaattgtgct     8820 gttttatcct ttaccttgtc tacaaacccc ttaaaaacgt tttaaaggc ttttaagccg     8880 tctgtacgtt ccttaagatc aacgtgatat aggtttgcta acctttgcgt tcacttaact    8940
```

```
aacttatagg ggtaacactt aaaaaagaat caataacgat agaaaccgct cctaaagcag    9000 gtgcatttttt tcctaacgaa gaaggcaata gttcacatttt attgtctaaa tgagaatgga    9060
ctctagaaga aacttcgttt ttaatcgtat ttaaaacaat gggatgagat tcaattatat    9120
gatttctcaa gataacagct tctatatcaa atgtattaag gatattggtt aatccaattc    9180
cgatataaaa gccaaagttt tgaagtgcat ttaacatttc tacatcattt ttatttgcgc    9240
gttccacaat ctcttttcga gaatattct ttttcttctt agagagcgaa gccagtaacg    9300 cttttttcaga agcatataat tcccaacagc ctcgatttcc acagctgcat ttgggtccat    9360
taaaatctat cgtcatatga cccatttccc cagaaaaacc ctgaacacct ttatacaatt    9420
cgttgttaat aacaagtcca gttccaattc cgatattaat actgatgtaa acgatgtttt    9480
catagttttt tgtcatacca aatacttttt caccgtatgc tcctgcatta gcttcatttt    9540
caacaaaaac cggaacatta aactcactct caattaaaaa ctgcaaatct ttgatattcc    9600
aatttaagtt aggcatgaaa ataatttgct gatgacgatc tacaaggcct ggaacacaaa    9660
ttcctattcc gactagacca taaggggact caggcatatg ggttacaaaa ccatgaataa    9720
gtgcaaataa aatctctttt acttc    9745

<210> SEQ ID NO 2
<211> LENGTH: 482
<212> TYPE: PRT
<213> ORGANISM: Bos taurus

<400> SEQUENCE: 2

Met Ala Ser Thr Lys Thr Pro Arg Pro Tyr Ser Glu Ile Pro Ser Pro
1               5                   10                  15

Gly Asp Asn Gly Trp Leu Asn Leu Tyr His Phe Trp Arg Glu Lys Gly
                20                  25                  30

Ser Gln Arg Ile His Phe Arg His Ile Glu Asn Phe Gln Lys Tyr Gly
            35                  40                  45

Pro Ile Tyr Arg Glu Lys Leu Gly Asn Leu Glu Ser Val Tyr Ile Ile
        50                  55                  60

His Pro Glu Asp Val Ala His Leu Phe Lys Phe Glu Gly Ser Tyr Pro
65                  70                  75                  80

Glu Arg Tyr Asp Ile Pro Pro Trp Leu Ala Tyr His Arg Tyr Tyr Gln
                85                  90                  95

Lys Pro Ile Gly Val Leu Phe Lys Lys Ser Gly Thr Trp Lys Lys Asp
            100                 105                 110

Arg Val Val Leu Asn Thr Glu Val Met Ala Pro Glu Ala Ile Lys Asn
        115                 120                 125

Phe Ile Pro Leu Leu Asn Pro Val Ser Gln Asp Phe Val Ser Leu Leu
    130                 135                 140

His Lys Arg Ile Lys Gln Gln Gly Ser Gly Lys Phe Val Gly Asp Ile
145                 150                 155                 160

Lys Glu Asp Leu Phe His Phe Ala Phe Glu Ser Ile Thr Asn Val Met
                165                 170                 175

Phe Gly Glu Arg Leu Gly Met Leu Glu Glu Thr Val Asn Pro Glu Ala
            180                 185                 190

Gln Glu Phe Ile Asp Ala Val Tyr Lys Met Phe His Thr Ser Val Pro
        195                 200                 205

Leu Leu Asn Val Pro Pro Glu Leu Tyr Arg Leu Phe Arg Thr Lys Thr
    210                 215                 220

Trp Arg Asp His Val Ala Ala Trp Asp Thr Ile Phe Asn Lys Ala Glu
```

```
            225                 230                 235                 240
Lys Tyr Thr Glu Ile Phe Tyr Gln Asp Leu Arg Arg Lys Thr Glu Phe
                245                 250                 255

Arg Asn Tyr Pro Gly Ile Leu Tyr Cys Leu Lys Ser Glu Lys Met
                260                 265             270

Leu Leu Glu Asp Val Lys Ala Asn Ile Thr Glu Met Leu Ala Gly Gly
                275                 280                 285

Val Asn Thr Thr Ser Met Thr Leu Gln Trp His Leu Tyr Glu Met Ala
    290                 295                 300

Arg Ser Leu Asn Val Gln Glu Met Leu Arg Glu Val Leu Asn Ala
305                 310                 315                 320

Arg Arg Gln Ala Glu Gly Asp Ile Ser Lys Met Leu Gln Met Val Pro
                325                 330                 335

Leu Leu Lys Ala Ser Ile Lys Glu Thr Leu Arg Leu His Pro Ile Ser
                340                 345                 350

Val Thr Leu Gln Arg Tyr Pro Glu Ser Asp Leu Val Leu Gln Asp Tyr
                355                 360                 365

Leu Ile Pro Ala Lys Thr Leu Val Gln Val Ala Ile Tyr Ala Met Gly
    370                 375                 380

Arg Asp Pro Ala Phe Phe Ser Ser Pro Asp Lys Phe Asp Pro Thr Arg
385                 390                 395                 400

Trp Leu Ser Lys Asp Lys Asp Leu Ile His Phe Arg Asn Leu Gly Phe
                405                 410                 415

Gly Trp Gly Val Arg Gln Cys Val Gly Arg Arg Ile Ala Glu Leu Glu
                420                 425                 430

Met Thr Leu Phe Leu Ile His Ile Leu Glu Asn Phe Lys Val Glu Met
                435                 440                 445

Gln His Ile Gly Asp Val Asp Thr Ile Phe Asn Leu Ile Leu Thr Pro
                450                 455                 460

Asp Lys Pro Ile Phe Leu Val Phe Arg Pro Phe Asn Gln Asp Pro Pro
465                 470                 475                 480

Gln Ala

<210> SEQ ID NO 3
<211> LENGTH: 461
<212> TYPE: PRT
<213> ORGANISM: Bos taurus

<400> SEQUENCE: 3

Met Ser Thr Gln Glu Gln Thr Pro Gln Ile Cys Val Val Gly Ser Gly
1               5                   10                  15

Pro Ala Gly Phe Tyr Thr Ala Gln His Leu Leu Lys His His Ser Arg
                20                  25                  30

Ala His Val Asp Ile Tyr Glu Lys Gln Leu Val Pro Phe Gly Leu Val
            35                  40                  45

Arg Phe Gly Val Ala Pro Asp His Pro Glu Val Lys Asn Val Ile Asn
    50                  55                  60

Thr Phe Thr Gln Thr Ala Arg Ser Asp Arg Cys Ala Phe Tyr Gly Asn
65                  70                  75                  80

Val Glu Val Gly Arg Asp Val Thr Val Gln Glu Leu Gln Asp Ala Tyr
                85                  90                  95

His Ala Val Val Leu Ser Tyr Gly Ala Glu Asp His Gln Ala Leu Asp
                100                 105                 110

Ile Pro Gly Glu Glu Leu Pro Gly Val Phe Ser Ala Arg Ala Phe Val
```

```
            115                 120                 125
Gly Trp Tyr Asn Gly Leu Pro Glu Asn Arg Glu Leu Ala Pro Asp Leu
130                 135                 140

Ser Cys Asp Thr Ala Val Ile Leu Gly Gln Gly Asn Val Ala Leu Asp
145                 150                 155                 160

Val Ala Arg Ile Leu Leu Thr Pro Pro Asp His Leu Glu Lys Thr Asp
                165                 170                 175

Ile Thr Glu Ala Ala Leu Gly Ala Leu Arg Gln Ser Arg Val Lys Thr
                180                 185                 190

Val Trp Ile Val Gly Arg Arg Gly Pro Leu Gln Val Ala Phe Thr Ile
                195                 200                 205

Lys Glu Leu Arg Glu Met Ile Gln Leu Pro Gly Thr Arg Pro Met Leu
210                 215                 220

Asp Pro Ala Asp Phe Leu Gly Leu Gln Asp Arg Ile Lys Glu Ala Ala
225                 230                 235                 240

Arg Pro Arg Lys Arg Leu Met Glu Leu Leu Arg Thr Ala Thr Glu
                245                 250                 255

Lys Pro Gly Val Glu Glu Ala Ala Arg Arg Ala Ser Ala Ser Arg Ala
                260                 265                 270

Trp Gly Leu Arg Phe Phe Arg Ser Pro Gln Gln Val Leu Pro Ser Pro
                275                 280                 285

Asp Gly Arg Arg Ala Ala Gly Ile Arg Leu Ala Val Thr Arg Leu Glu
                290                 295                 300

Gly Ile Gly Glu Ala Thr Arg Ala Val Pro Thr Gly Asp Val Glu Asp
305                 310                 315                 320

Leu Pro Cys Gly Leu Val Leu Ser Ser Ile Gly Tyr Lys Ser Arg Pro
                325                 330                 335

Ile Asp Pro Ser Val Pro Phe Asp Pro Lys Leu Gly Val Val Pro Asn
                340                 345                 350

Met Glu Gly Arg Val Val Asp Val Pro Gly Leu Tyr Cys Ser Gly Trp
                355                 360                 365

Val Lys Arg Gly Pro Thr Gly Val Ile Thr Thr Thr Met Thr Asp Ser
370                 375                 380

Phe Leu Thr Gly Gln Ile Leu Leu Gln Asp Leu Lys Ala Gly His Leu
385                 390                 395                 400

Pro Ser Gly Pro Arg Pro Gly Ser Ala Phe Ile Lys Ala Leu Leu Asp
                405                 410                 415

Ser Arg Gly Val Trp Pro Val Ser Phe Ser Asp Trp Glu Lys Leu Asp
                420                 425                 430

Ala Glu Glu Val Ser Arg Gly Gln Ala Ser Gly Lys Pro Arg Glu Lys
                435                 440                 445

Leu Leu Asp Pro Gln Glu Met Leu Arg Leu Leu Gly His
450                 455                 460

<210> SEQ ID NO 4
<211> LENGTH: 109
<212> TYPE: PRT
<213> ORGANISM: Bos taurus

<400> SEQUENCE: 4

Met Ser Ser Ser Glu Asp Lys Ile Thr Val His Phe Ile Asn Arg Asp
1               5                   10                  15

Gly Glu Thr Leu Thr Thr Lys Gly Lys Ile Gly Asp Ser Leu Leu Asp
                20                  25                  30
```

```
Val Val Val Gln Asn Asn Leu Asp Ile Asp Gly Phe Gly Ala Cys Glu
         35              40              45

Gly Thr Leu Ala Cys Ser Thr Cys His Leu Ile Phe Glu Gln His Ile
     50              55              60

Phe Glu Lys Leu Glu Ala Ile Thr Asp Glu Glu Asn Asp Met Leu Asp
65              70              75              80

Leu Ala Tyr Gly Leu Thr Asp Arg Ser Arg Leu Gly Cys Gln Ile Cys
             85              90              95

Leu Thr Lys Ala Met Asp Asn Met Thr Val Arg Val Pro
            100             105
```